US008899749B2

(12) United States Patent
Imamura

(10) Patent No.: US 8,899,749 B2
(45) Date of Patent: Dec. 2, 2014

(54) IMAGE PROCESSING APPARATUS, IMAGE PROCESSING METHOD, IMAGE PROCESSING SYSTEM, SLO APPARATUS, AND PROGRAM

(75) Inventor: Hiroshi Imamura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 174 days.

(21) Appl. No.: 13/399,790

(22) Filed: Feb. 17, 2012

(65) Prior Publication Data

US 2012/0218515 A1 Aug. 30, 2012

(30) Foreign Application Priority Data

Feb. 25, 2011 (JP) .................................. 2011-040273

(51) Int. Cl.
*A61B 3/14* (2006.01)
*A61B 3/00* (2006.01)
*A61B 3/10* (2006.01)
*A61B 3/12* (2006.01)

(52) U.S. Cl.
CPC .................. *A61B 3/12* (2013.01); *A61B 3/1025* (2013.01); *A61B 3/14* (2013.01)
USPC .......................................... 351/206; 351/246

(58) Field of Classification Search
USPC .......................................................... 351/206
See application file for complete search history.

(56) References Cited

U.S. PATENT DOCUMENTS

2009/0303438 A1* 12/2009 Yamada et al. ............... 351/206
2011/0109911 A1* 5/2011 Podoleanu ..................... 356/451
2011/0234975 A1 9/2011 Hieose
2012/0133888 A1* 5/2012 Gray et al. .................... 351/206
2013/0169934 A1* 7/2013 Verdooner .................... 351/246

FOREIGN PATENT DOCUMENTS

WO 2009015295 A1 1/2009

OTHER PUBLICATIONS

Martin, Joy A. et al., "Pulsatility of parafoveal capillary leukocytes", Experimental Eye Research 88 (2009) 356-360, journal homepage: www.elsevier.com/locate/yexer.
Martin, Joy A. et al.,"Direct and Noninvasive Assessment of Parafoveal Capillary Leukocyte Velocity", 2005 by the American Academy of Ophthalmology, vol. 112, No. 12, Published by Elsevier Inc.,ISSN 0161-6420/05, pp. 1219-2224.
Tam, Johnny et al.,"Enhanced Detection of Cell Paths in Spatiotemporal Plots for Noninvasive Microscopy of the Human Retina", 978-1-4244-4126-6/10/ 2010 IEEE, pp. 584-587.
Tam, Johnny et al.,"Noninvasive Visualization and Analysis of Parafoveal Capillaries in Humans", Investigative Ophthalmology & Visual Science, Mar. 2010, vol. 51, No. 3, Association for Research in Vision and Ophthalmology, pp. 1691-1698.

* cited by examiner

*Primary Examiner* — Jordan Schwartz
(74) *Attorney, Agent, or Firm* — Canon U.S.A., Inc. IP Division

(57) ABSTRACT

An image processing apparatus includes an SLO image acquisition unit configured to acquire a plurality of SLO images obtainable by an SLO apparatus that scans a target to be captured with signal light at various focus positions in an optical axis direction of the signal light. The image processing apparatus includes a structure acquisition unit configured to acquire a specific structure of the target to be captured. The image processing apparatus includes an object image acquisition unit configured to acquire an image of the specific structure from each of the plurality of SLO images captured at various focus positions according to the specific structure.

13 Claims, 14 Drawing Sheets

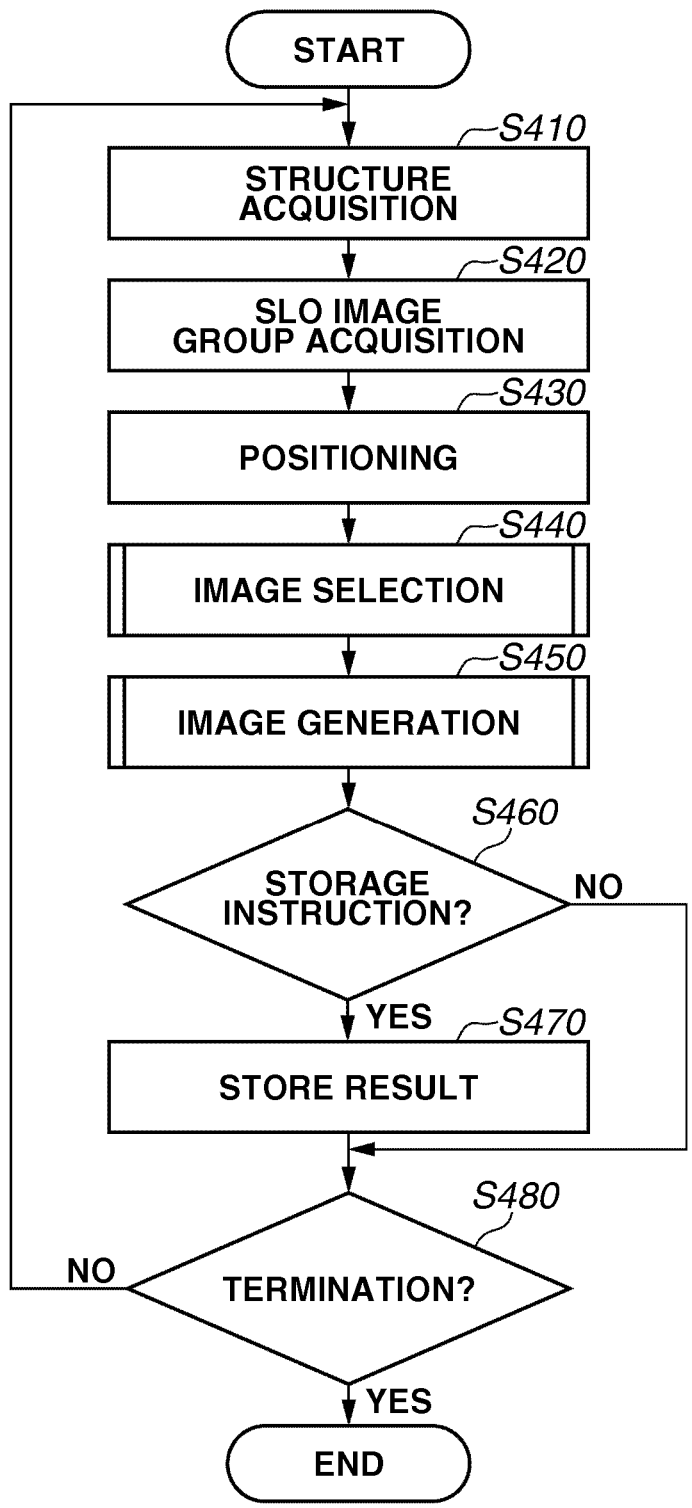

IMAGE PROCESSING APPARATUS, IMAGE PROCESSING METHOD, IMAGE PROCESSING SYSTEM, SLO APPARATUS, AND PROGRAM

TECHNICAL FIELD

The present disclosure relates to an image processing apparatus that acquires a predetermined image from a captured SLO image, an image processing method, and an SLO apparatus that executes the image processing.

BACKGROUND

A scanning laser ophthalmoscope (SLO), which is an ophthalmologic apparatus operable based on the principle of confocal laser microscope, is an apparatus that can perform raster scanning on an eyeground with a laser (i.e., a measuring beam) and can speedily obtain a high-resolution planar image of the eyeground based on the intensity of an optical feedback of the laser. Hereinafter, an apparatus capable of capturing a planar image is referred to as an SLO apparatus.

Further, there is a conventional AO-SLO apparatus including an adaptive optics (AO) system, which performs real-time measurement of an aberration of an eye to be tested with a wavefront sensor and corrects an aberration of a measuring beam or its optical feedback generated at the eye to be tested with a wavefront correction device. The AO-SLO apparatus can acquire a planar image that is excellent in horizontal resolution.

The planar image having excellent horizontal resolution can be used, for example, to extract a retinal blood vessel or a blood cell to observe a blood cell state, or measure the thickness of a nerve fiber bundle to evaluate the disorder of a ganglion cell. Further, the planar image can be used to evaluate visual functions, or measure a density distribution (or alignment) of photoreceptor cells.

A conventional technique capable of obtaining an image of a specific structure, such as organization, cell, or lesion, with an SLO apparatus is discussed in Johnny Tam, et. al., Noninvasive Visualization and analysis of Parafoveal Capillaries in Humans, Investigative Ophthalmology & Visual Science, March 2010, Vol. 51, No. 3, pp 1691-1698. The conventional technique includes setting shooting conditions (e.g., wavelength of signal light) for the SLO apparatus, capturing an image of an area including a macula area, and acquiring an image of a capillary vessel based on the obtained image.

When a single SLO image is obtained by scanning an observation target with signal light having a fixed focus position, the captured image may not include the structure of the observation target. An operator cannot use such a defective image to observe a target structure. Accordingly, the operator is required to change the settings and perform a shooting operation again. Thus, the efficiency of the shooting operation for each tested person deteriorates significantly.

SUMMARY

An image processing apparatus according to an present embodiment includes an SLO image acquisition unit configured to acquire a plurality of SLO images obtainable by an SLO apparatus that scans a target to be captured with signal light at various focus positions in an optical axis direction of the signal light, a structure acquisition unit configured to acquire a specific structure of the target to be captured, and an object image acquisition unit configured to acquire an image of the specific structure from each of the plurality of SLO images captured at various focus positions according to the specific structure.

Further features and aspects of the present embodiment will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, and features together with the description, serve to explain the principles of the embodiments.

FIG. 4 is a flowchart illustrating example processing that can be performed by the image processing apparatus.

FIGS. 5A to 5D illustrate example images that can be obtained by the processing according to the first exemplary embodiment, in which FIG. 5A illustrates an OCT tomographic image of a normal eye part, FIG. 5B illustrates an OCT tomographic image of an eye part that has abnormality in structure, FIG. 5C illustrates a group of SLO images, and FIG. 5D illustrates an image of a specific structure generated from the SLO image group.

FIGS. 11A to 11C illustrate an OCT tomographic image acquisition method that can be realized by the composite apparatus according to the second exemplary embodiment, in which FIG. 11A illustrates signal light that reaches a retina of an eye to be tested, FIG. 11B illustrates a signal light scanning mechanism, and FIG. 11C illustrates an acquired tomographic image.

FIGS. 13A to 13C illustrate example images that can be obtained through the processing according to the second exemplary embodiment, in which FIG. 13A illustrates an OCT tomographic image of a normal eye part, FIG. 13B illustrates a group of SLO images, and FIG. 13C illustrates an image of a specific structure generated based on the SLO image group.

FIGS. 14A to 14D illustrates images that can be obtained by the processing according to a third exemplary embodiment, in which FIG. 14A illustrates an OCT tomographic image of a normal structure, FIG. 14B illustrates a group of SLO images, FIG. 14C illustrates a still image of a specific structure generated based on the SLO image group, and FIG. 14D illustrates a moving image generated based on the SLO image group.

DESCRIPTION OF THE EMBODIMENTS

Various exemplary embodiments, and features will be described in detail below with reference to the drawings.

Exemplary embodiments are described in detail with reference to the attached drawings.

An image processing apparatus according to a first exemplary embodiment can generate or select an SLO image that follows a specific structure based on a group of SLO images captured as various focus positions and stored in a storage apparatus. The medical cases according to the present exemplary embodiment include aged macular degeneration (AMD) and polypoidal choroidal sculopathy (PCV) in the broad sense. An example observation target is a photoreceptor cell.

A photoreceptor cell layer (i.e., a distribution range of the photoreceptor cell) extends from an external limiting membrane (ELM, a portion slightly closer to an anterior eye part (i.e., an inner layer) than an interface between inner and outer segments of the photoreceptors (IS/OS)) to an anterior eye part boundary of a retinal pigment epithelium (RPE). The IS/OS is present at substantially the center (more specially, the boundary between the inner and outer segments) of the photoreceptor cell layer. Therefore, an image captured along the IS/OS includes an image of the photoreceptor cell.

Figure 1:
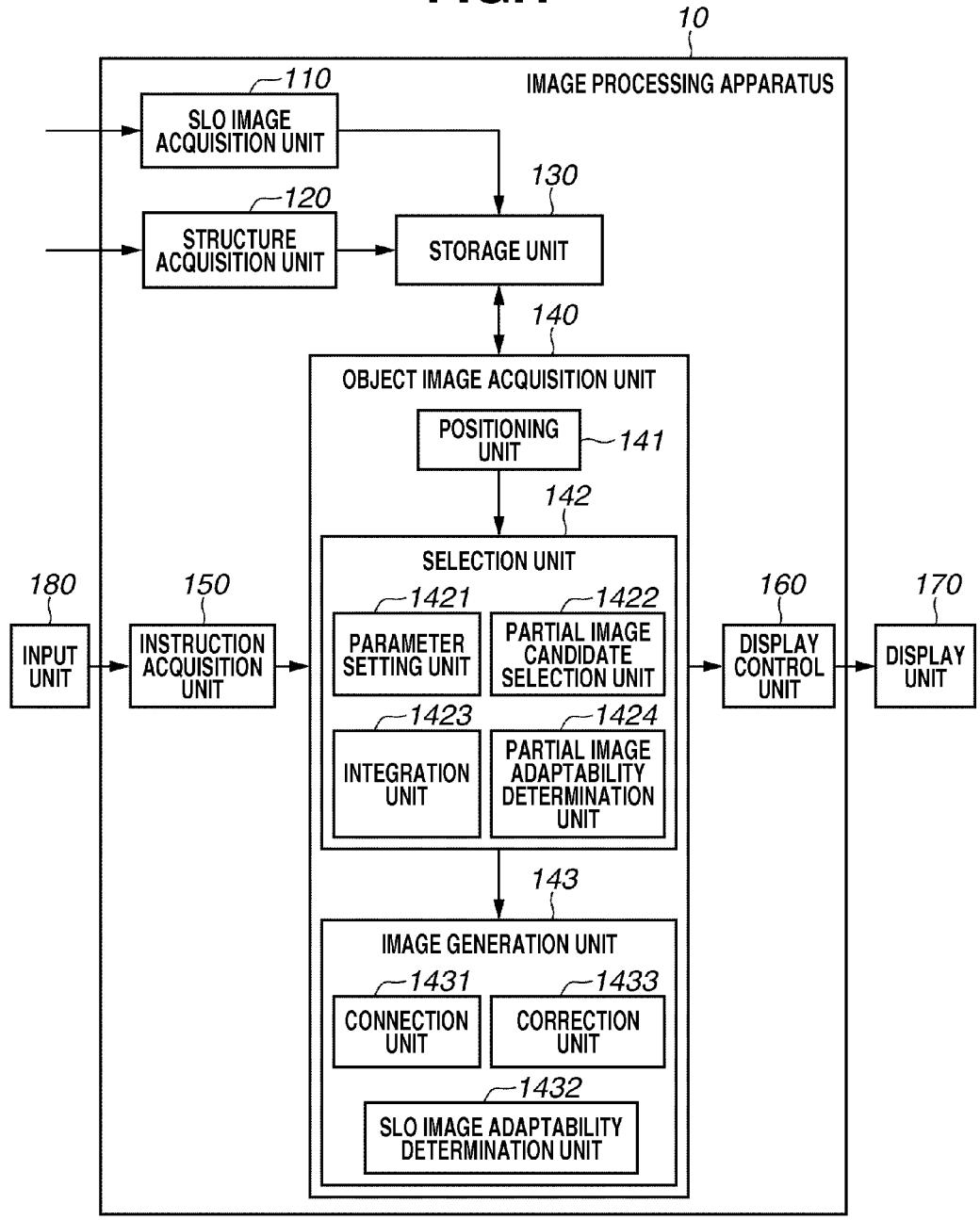
FIG. 1 illustrates an example of a functional configuration of an image processing apparatus according to a first exemplary embodiment.

A functional configuration of an image processing apparatus 10 according to the present exemplary embodiment is described in detail below with reference to FIG. 1. FIG. 1 is a block diagram illustrating a functional configuration of the image processing apparatus 10. The image processing apparatus 10 includes an SLO image acquisition unit 110, a structure acquisition unit 120, a storage unit 130, an object image acquisition unit 140, and an instruction acquisition unit 150.

The SLO image acquisition unit 110 can acquire a group of SLO images captured beforehand by an SLO apparatus at various focus positions and stored in a storage apparatus.

More specifically, the focus position of each acquired SLO image is different in the depth direction (i.e., the direction of the optical axis of the signal light of the SLO apparatus). In a case where the target to be captured is an eye part, the focus position of each image is variable due to involuntary eye movement during fixation, even when the focus position is set to remain the same. In the present exemplary embodiment, the focus position of each SLO image is different when the focus position is set to be different by the SLO apparatus. The influence of the involuntary eye movement during fixation is not taken into consideration.

When an eyeground to be captured is scanned with signal light having various focus positions, a plurality of SLO images differentiated in focus position can be obtained. An SLO image capturing apparatus 30 or the SLO apparatus is a scanning laser ophthalmoscope that includes an adaptive optics system capable of correcting mainly an aberration of an image that may be generated by signal light at the eye part.

The eyeground is a concept corresponding to an anterior eye part that is an area including the inside of a retina and a retina surface. The target to be captured is an area including or existing in the vicinity of a macula area of the eyeground. The SLO having an adaptive optics system can obtain an image of a capillary vessel in the vicinity of the macula retina, a nerve fiber, or a photoreceptor cell, which is smaller than a blood vessel to be captured as a target by a conventional Fourier domain OCT or a conventional eyeground camera.

The structure acquisition unit 120 can acquire the position of a specific structure or its three-dimensional shape, which is required to acquire an image of an observation target as structure features of an eyeground to be captured.

In the present exemplary embodiment, the observation target is the photoreceptor cell. Therefore, the structure acquisition unit 120 identifies the position of the interface between inner and outer segments of the photoreceptors (IS/OS) (i.e., the specific structure) included in the photoreceptor cell. The structure acquisition unit 120 captures an image of the photoreceptor cell based on the identified position of the interface between inner and outer segments of the photoreceptors (IS/OS).

The structure features include a layer structure of the organization and a lesion. The structure features can be identified by analyzing a group of tomographic images of an eyeground captured by an OCT imaging apparatus. Alternatively, the image processing apparatus 10 can acquire information indicating the position and the shape of a predetermined structure from a data server 50, instead of analyzing the OCT tomographic images.

The storage unit 130 stores various parameters that have been determined beforehand or input for image processing.

The object image acquisition unit 140 can obtain an image of a specific structure based on a group of SLO images according to the specific structure. The object image acquisition unit 140 includes a positioning unit 141, a selection unit 142, and an image generation unit 143. The selection unit 142 includes a parameter setting unit 1421, a partial image candidate selection unit 1422, an integration unit 1423, and a partial image adaptability determination unit 1424. Further, the image generation unit 143 includes a connection unit 1431, an SLO image adaptability determination unit 1432, and a correction unit 1433.

When the shape of the photoreceptor cell layer is not deformed so much compared to a normal structure, the object image acquisition unit 140 selects an optimum SLO image best focused on the photoreceptor cell (boundary) layer from the SLO image group. In other words, the object image acquisition unit 140 can obtain an image easy to observe the photoreceptor cell from a plurality of SLO images captured at various focus positions in the optical axis direction of the signal light.

On the other hand, when the shape of the photoreceptor cell layer is greatly curved or bent compared to a normal state, a single SLO image obtained with signal light having a fixed focus position may not include the structure of an observation target, so that an operator cannot observe the subject structure.

Hence, the object image acquisition unit 140 selects a plurality of partial images whose focus positions are set to be adjacent to the photoreceptor cell layer boundary at each position on the eyeground, from the SLO images, and generates a new SLO image by connecting the selected partial images. Thus, even when the shape of the photoreceptor cell layer is deformed greatly and only a part of the structure is included in a single SLO image, an operator can easily observe or analyze the photoreceptor cell in the imaging range.

Further, compared to a case where an SLO image corresponding to each of a plurality of fixed focus positions is obtained and an SLO image is obtained by changing the focus position along a specific structure, the image processing apparatus according to the present exemplary embodiment can prevent the scanning time from increasing due to a change of the focus position. Thus, it is feasible to prevent the image quality from deteriorating while reducing the influence of the involuntary eye movement during fixation.

A display control unit 160 can perform control for causing a display unit 170 to display an image of a specific structure obtained by the object image acquisition unit 140. The display unit 170 can display the image of the specific structure. An input unit 180 receives an instruction input from a user and supplies the received instruction to the image processing apparatus 10.

Figure 2:
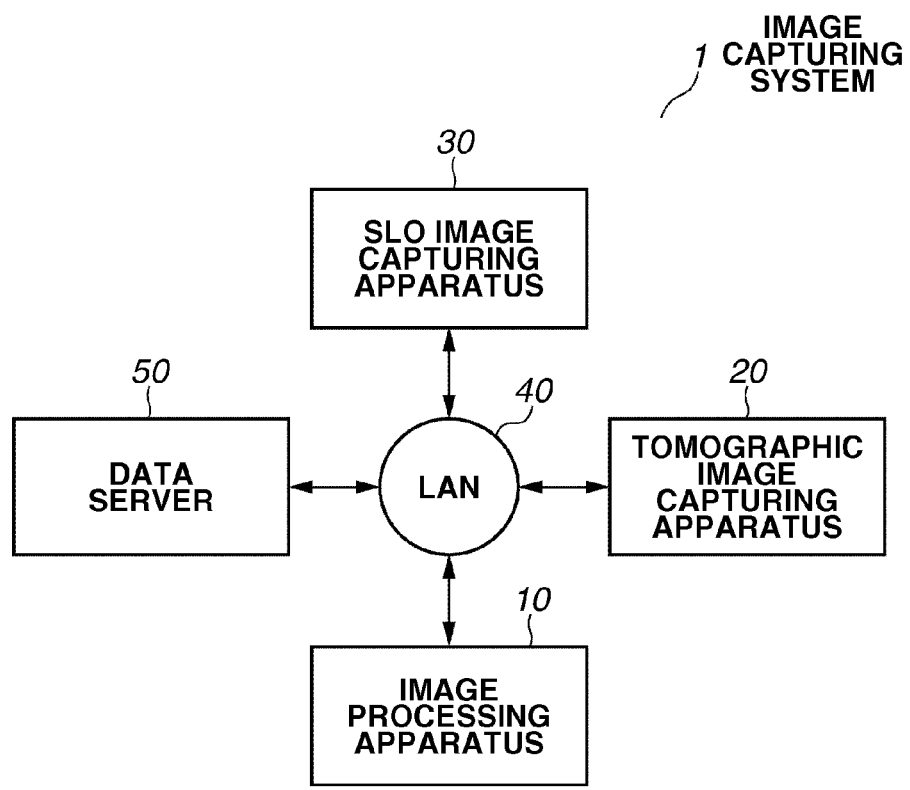
FIG. 2 is a block diagram illustrating an example configuration of an image capturing system 1 that includes the image processing apparatus.

An image capturing system 1 including the above-described image processing apparatus 10 is described below with reference to FIG. 2. FIG. 2 illustrates an example configuration of a diagnostic imaging system that includes the image processing apparatus 10 according to the present exemplary embodiment. As illustrated in FIG. 2, the image processing apparatus 10 is connected to a tomographic image capturing apparatus 20, the SLO image capturing apparatus 30, and the data server 50, via a local area network (LAN) 40, which can be constructed by an optical fiber, a universal serial bus (USB), or IEEE1394. The LAN can be replaced by an external network (e.g., Internet) via which respective apparatuses of the system can be connected to each other.

The tomographic image capturing apparatus 20 is an apparatus capable of capturing a volume image of an eyeground part. For example, the tomographic image capturing apparatus 20 is a time-domain or Fourier domain optical coherence tomography apparatus (OCT apparatus). The tomographic image capturing apparatus 20 captures a three-dimensional tomographic image of an eye to be tested according to an operation of an operator (not illustrated). The obtained volume image can be transmitted to the image processing apparatus 10 and the data server 50.

The SLO image capturing apparatus 30 is an apparatus that can capture a planar image (SLO image) of an eyeground part. The SLO image capturing apparatus 30 captures a plurality of SLO images at various focus positions and transmits the captured plurality of SLO images to the image processing apparatus 10 and the data server 50.

The data server 50 is a server that can store volume images and SLO images of each eye to be tested, and features of eyeground part (hereinafter, eye part features) as described below. The data stored in the data server 50 includes volume images of an eye to be tested output from the tomographic image capturing apparatus 20, a plurality of SLO images output from the SLO image capturing apparatus 30, and eye part features output from the image processing apparatus 10.

Further, the data server 50 transmits the data relating to the eye to be tested (e.g., volume images, SLO images, and eye part features) and the data representing normal values of eye part features to the image processing apparatus 10 in response to a request from the image processing apparatus 10. In the present exemplary embodiment, when the features and the structure are normal, it means that the eye part is not diseased at all. When the layer structure of a retina is normal, it means that the retina is composed of a plurality of flat layers. On the other hand, if a layer of the retina swells at least partly, it is generally understood that the layer structure is not normal.

Figure 3:
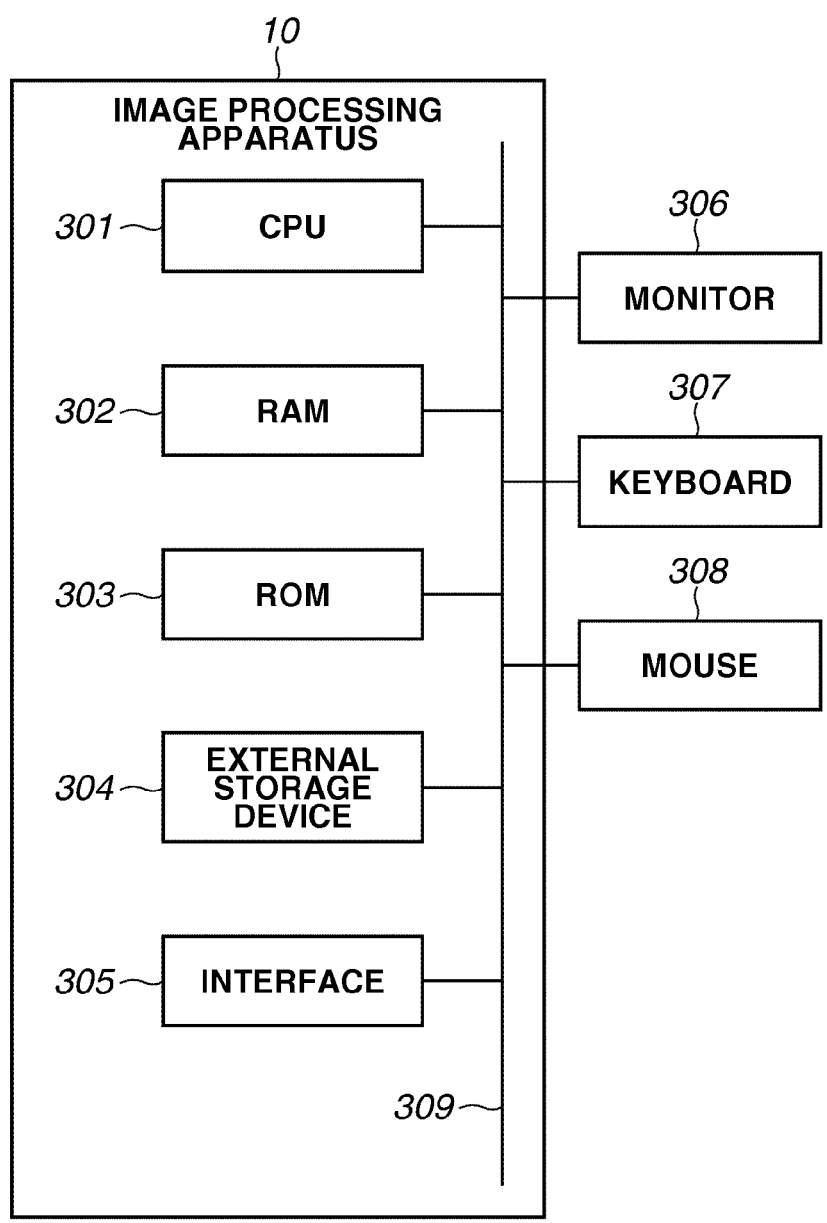
FIG. 3 is a block diagram illustrating an example hardware configuration of the image processing apparatus.

An example hardware configuration of the image processing apparatus 10 that has the above-described functional configuration is described with reference to FIG. 3. The image processing apparatus 10 illustrated in FIG. 3 includes a central processing unit (CPU) 301, a memory (RAM) 302, a control memory (ROM) 303, a storage device 304, and an interface 305. The image processing apparatus 10 is connected to a monitor 306, a keyboard 307, and a mouse 308.

A control program required for the CPU 301 to realize image processing functions according to the present exemplary embodiment and data to be used when the CPU 301 executes the control program are stored in the storage device 304. The control program and the data can be appropriately loaded into the RAM 302 via a bus 309 from the storage device 304. When the CPU 301 executes the control program, the CPU 301 can realize each of the above-described functions in cooperation with the above-described hardware.

For example, the storage device 304 is functionally operable as the storage unit 130 illustrated in FIG. 1. The keyboard 307 or the mouse 308 is functionally operable as the input unit 180 illustrated in FIG. 1. The monitor 306 is functionally operable as the display unit 170 illustrated in FIG. 1. Further, the image processing apparatus 10 can realize the following processing.

Example processing that can be executed by the image processing apparatus 10 having the above-described configuration is described below with reference to a flowchart illustrated in FIG. 4.

<Step S410>

In step S410, the structure acquisition unit 120 acquires feature structure data of an eye part from a volume image. In the present exemplary embodiment, the target to be captured is an eyeground. Especially, an interface between inner and outer segments of the photoreceptors is designated as a special observation target by the instruction acquisition unit 150.

More specifically, as fundamental structure features of the eyeground (i.e., the target to be captured), the structure acquisition unit 120 acquires the position or the shape of each of an inner limiting membrane B1, a nerve fiber layer boundary B2, an inner plexiform layer boundary B4, an interface between inner and outer segments of the photoreceptors B5, an outer boundary of the retinal pigment epithelium B6, and a retinal blood vessel area V in each eye part volume image.

The photoreceptor cell of the observation target can be obtained from the interface between inner and outer segments of the photoreceptors B5. Further, the structure acquisition unit 120 identifies the position of a macula area. It is useful that the structure acquisition unit 120 acquires a volume image of an area including the macula area beforehand.

Further, the structure acquisition unit 120 stores the acquired data representing the eye part features in the storage unit 130 and transmits the stored data to the data server 50 if required. These feature data can be used to obtain a photoreceptor cell image as described below.

An example procedure for acquiring eye part features is described. First, an image processing method for detecting a boundary of layers is described below. In the present exemplary embodiment, a volume image (i.e., a target to be processed) is regarded as an assembly of two-dimensional tomographic images (B scanning images). The structure acquisition unit 120 performs the following processing on each two-dimensional tomographic image.

First, the structure acquisition unit 120 performs smoothing processing on a target two-dimensional tomographic image to remove noise components. Next, the structure acquisition unit 120 detects edge components from the acquired two-dimensional tomographic image and extracts a plurality of line segments as candidates of layer boundaries with reference to the continuity thereof.

Then, the structure acquisition unit 120 selects the uppermost candidate line segment as the inner limiting membrane B1, the second uppermost candidate line segment as the nerve fiber layer boundary B2, and the third uppermost candidate line segment as the inner plexiform layer boundary B4. Further, the structure acquisition unit 120 selects a line segment having a maximum contrast, which is present on the outside of the inner limiting membrane B1 (i.e., in the larger z-coordinate value region in FIG. 5A), as the interface between inner and outer segments of the photoreceptors B5.

The structure acquisition unit 120 selects a line segment existing outside the interface between inner and outer segments of the photoreceptors B5 as an outer plexiform layer boundary. Further, the structure acquisition unit 120 selects the lowermost line segment of the layer boundary candidate group as the retinal pigment epithelium layer boundary B6.

Further, it is useful that the structure acquisition unit 120 performs precise extraction using the above-described line segments as initial values based on an applied variable shape model (e.g., Snakes or level set approach). Further, it is useful that the structure acquisition unit 120 detects layer boundaries according to a graph-cut method.

Further, the structure acquisition unit 120 can three-dimensionally execute the boundary detection on a volume image using the variable shape model or graph-cut, or can two-dimensionally execute the boundary detection on each two-dimensional tomographic image. Any other method capable of detecting layer boundaries from a tomographic image of an eye part is employable.

Next, the structure acquisition unit 120 can detect the retinal blood vessel area V from a retinal inner layer (not illustrated). More specifically, the structure acquisition unit 120 generates a projection image by integrating pixel values of the retinal inner layer along the depth direction. The structure acquisition unit 120 detects the retinal blood vessel area V from the generated projection image using an arbitrary line emphasis filter. The blood vessel information is usable in the positioning of an OCT tomographic image and an SLO image.

<Step S420>

In step S420, the SLO image acquisition unit 110 requests the data server 50 to transmit an SLO image group of a predetermined eye to be tested. The SLO image group includes a group of SLO images captured by the SLO image capturing apparatus 30 with signal light having various focus positions in the optical axis of the signal light.

Although the scanning area by the signal light remains the same or overlaps with each other, the imaging plane is variable in the depth direction. The data server 50 stores a plurality of SLO images captured at various focus positions for each eye to be tested.

Figure 5A:
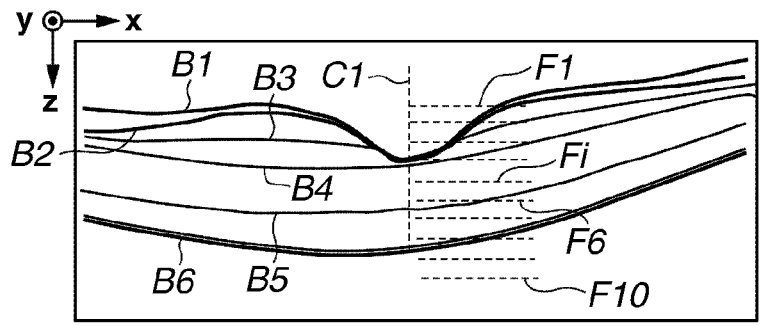
Figure 5B:
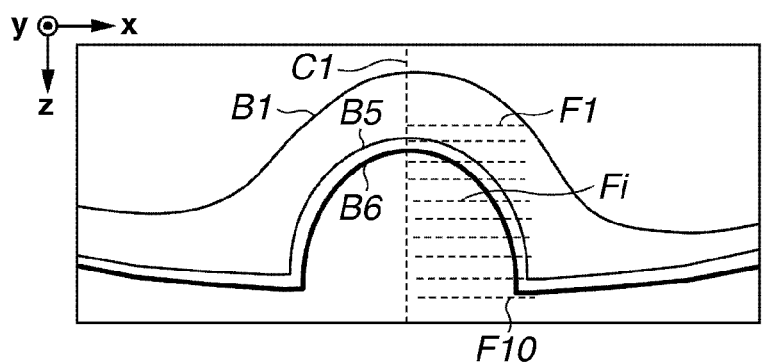

The SLO image acquisition unit 110 acquires the SLO image group via the LAN 40. In the present exemplary embodiment, as illustrated in FIG. 5B, the SLO image group acquired by the SLO image acquisition unit 110 includes a group of SLO images (10 sheets in total) captured by shifting the focus position (at the imaging center) stepwise at intervals of 20 μm from the interface between inner and outer segments of the photoreceptors. The SLO image acquisition unit 110 stores the acquired SLO image group in the storage unit 130 of the image processing apparatus 10.

<Step S430>

In step S430, the positioning unit 141 adjusts the positional relationship between the coordinate system of the SLO image group and the data representing the eye part features. As the position (x, y) of the retinal blood vessel area V is already obtained in each coordinate system, the positioning unit 141 obtains parameters required for the positioning, such as translation (x, y), rotation, and enlargement rate, so that corresponding coordinate points coincide with each other.

The positioning unit 141 can use an arbitrary positioning method. In the present exemplary embodiment, the positioning unit 141 performs positioning based on the affine conversion. It is now assumed that the position of the blood vessel is identified beforehand on the acquired SLO image.

<Step S440>

In step S440, the selection unit 142 obtains an image that follows the distribution of the photoreceptor cell (i.e., the observation target) from a plurality of SLO images captured at various focus positions. If the interface between inner and outer segments of the photoreceptors has a deformed portion in the structure thereof, the selection unit 142 selects a partial image that fits the observation target at each position (x, y) of the SLO image based on the distribution of eye part features (including the layer boundaries and the retinal blood vessel area V).

In the present exemplary embodiment, the partial image is composed of one pixel. The selection unit 142 determines that the partial image fits the observation target if they coincide with each other in focus position, for example, if the distance from each position (x0, y0, z0) of a specific structure in the z direction is at least within a predetermined value.

If there is a plurality of partial images that fit the observation target, the integration unit 1423 integrates the partial images to acquire an integrated partial image. If the adaptability is determined for a single partial image, image features (e.g., distribution of eye part features, S/N ratio, and luminance distribution (such as contrast)) of a partial image candidate can be used as adaptability indices to select a partial image.

When the selection unit 142 performs the selection of a partial image based on the focus position and the image features, the selection unit 142 can obtain a partial image having excellent image quality while eliminating any image having deteriorated image quality due to the influence of the involuntary eye movement during fixation even when it is similar in focus position.

Through the processing in step S440, the selection unit 142 can obtain a partial image selected from any one of the SLO images captured at various coordinate positions (x, y). The processing to be performed in step S440 is described in detail below with reference to a flowchart illustrated in FIG. 6.

<Step S450>

In step S450, the image generation unit 143 generates a new SLO image candidate by connecting partial images (candidates) on respective x-y coordinate positions selected in step S440. In the present exemplary embodiment, if there is a plurality of partial image candidates at an x-y coordinate position, the image generation unit 143 generates an SLO image candidate as a combination of these partial images. The image generation unit 143 determines the adaptability of the entire SLO image and generates, as a new SLO image, an SLO image candidate having highest adaptability.

If no partial image is selected and the selection unit 142 selects one SLO image from the SLO image group, the image generation unit 143 does not connect partial images. The above-described processing is described in detail below with reference to a flowchart illustrated in FIG. 7.

<Step S460>

In step S460, the instruction acquisition unit 150 acquires an instruction from an external device to determine whether to store a newly generated image of the photoreceptor cell in the data server 50. For example, an operator can input a storage instruction via the keyboard 307 or the mouse 308. If the instruction acquisition unit 150 receives the storage instruction, the processing proceeds to step S470. If the instruction acquisition unit 150 does not receive the storage instruction, the processing proceeds to step S480.

<Step S470>

In step S470, the object image acquisition unit 140 transmits the newly generated SLO image together with associated information (e.g., inspection date and time, and information identifying an eye to be tested) to the data server 50. Further, the display control unit 160 causes the display unit 170 to display the image acquired by the object image acquisition unit 140.

<Step S480>

In step S480, the instruction acquisition unit 150 acquires an instruction from an external device to determine whether to terminate the SLO image generation processing by the image processing apparatus 10. For example, an operator can input a processing termination instruction via the input unit 180. If the instruction acquisition unit 150 receives the processing termination instruction, the instruction acquisition unit 150 terminates the analysis processing. On the other hand, if the instruction acquisition unit 150 receives a processing continuation instruction, the processing returns to step S410 in which the instruction acquisition unit 150 starts processing for the next eye to be tested or restarts the processing for the same eye.

Example images obtained through the above-described processing is described in detail below with reference to FIGS. 5A to 5D. FIGS. 5A and 5B illustrate OCT tomographic images including a fovea centralis C1 (macula retina) of an eyeground retina obtained by the tomographic image capturing apparatus 20. In each of FIGS. 5A and 5B, a plane extending in the x direction and the y direction is parallel to the eyeground. The z direction represents the depth direction of the eyeground and is substantially parallel to the optical axis of the signal light.

The structure acquisition unit 120 can identify the positions of respective layers (i.e., the inner limiting membrane B1, the nerve fiber layer boundary B2, the inner plexiform layer boundary B4, the interface between inner and outer segments of the photoreceptors B5, and the outer boundary of the retinal pigment epithelium B6). Further, F1 through F10 represent the imaging positions of SLO images.

The OCT tomographic image illustrated in FIG. 5A includes a macula retina region that is relatively normal. The OCT tomographic image illustrated in FIG. 5B includes a greatly curved interface between inner and outer segments of the photoreceptors due to the abnormality in region including the macula retina. In a case where there is not any curve or bending (see FIG. 5A), the selection unit 142 selects the SLO image captured at the position adjacent to the interface between inner and outer segments of the photoreceptors B5 (see F6) from the group of SLO images captured at various focus positions.

On the other hand, in a case where there is a large deformation (bending or curve) as illustrated in FIG. 5B, the selection unit 142 extracts partial images that include the interface between inner and outer segments of the photoreceptors B5 from the group of SLO images captured at various focus positions.

Figure 5C:
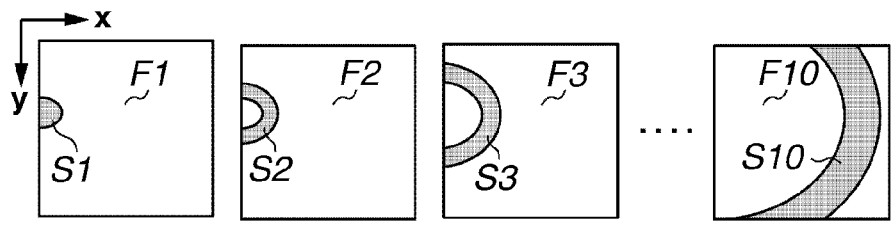

FIG. 5C illustrates the SLO images corresponding to the imaging positions F1 through F10. The SLO image positioned at the left side of FIG. 5C has the focus position adjacent to the front side. The selection unit 142 selects partial areas S1 through S10 that are focused on the interface between inner and outer segments of the photoreceptors, from these SLO images.

Figure 5D:
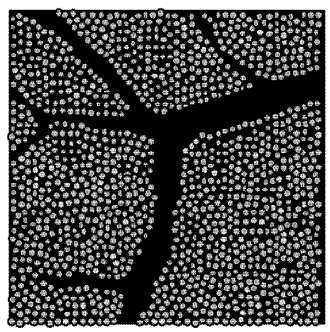

The image generation unit 143 combines the partial areas to obtain an integrated image of the photoreceptor cell as illustrated in FIG. 5D to enable an operator to confirm the flow path of a capillary vessel.

Figure 6:
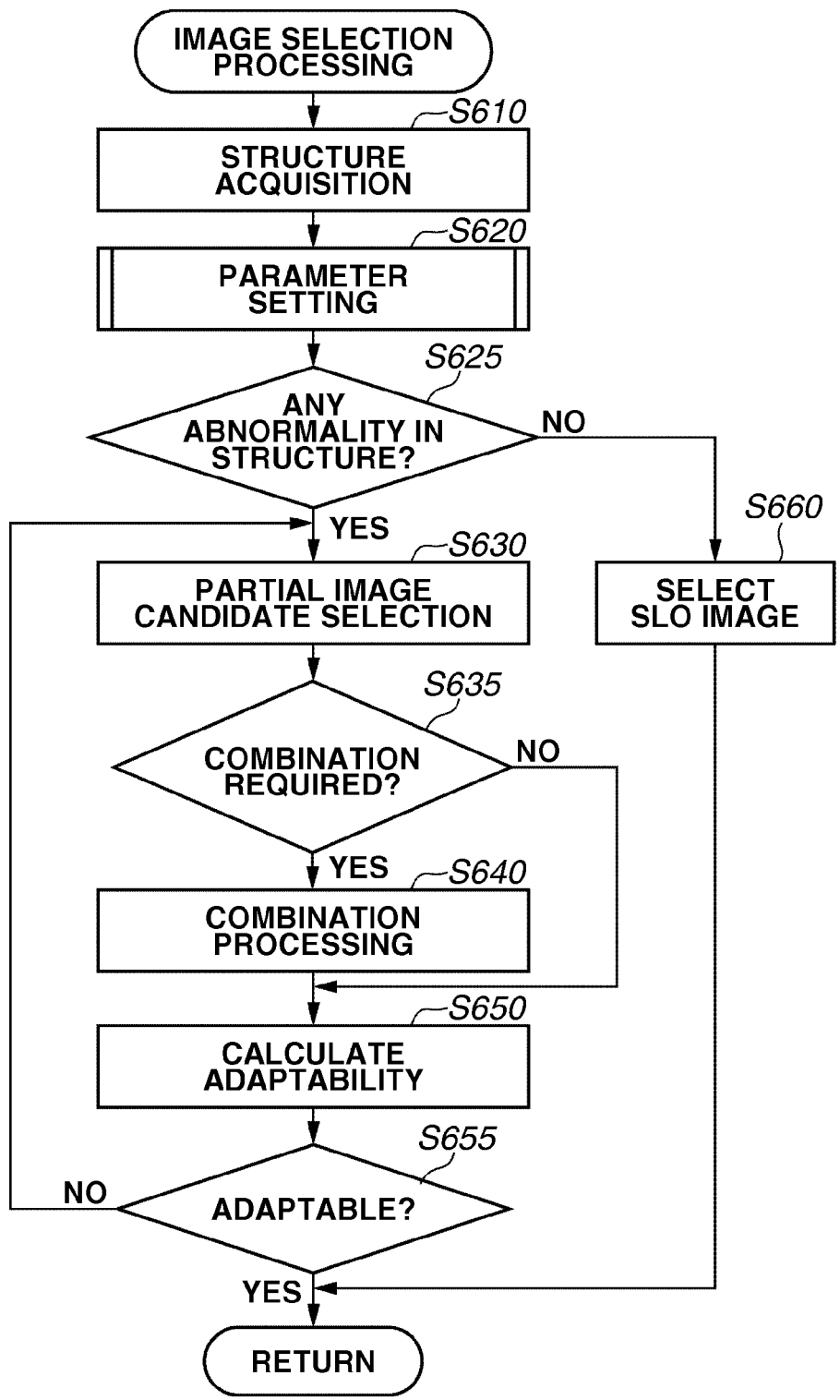
FIG. 6 is a flowchart illustrating an example of image selection processing that can be performed by a selection unit.

Next, an example of the processing to be performed in step S440 by the selection unit 142 is described in detail below with reference to the flowchart illustrated in FIG. 6.

<Step S610>

In step S610, the selection unit 142 acquires the eye part features (including the inner limiting membrane B1, the nerve fiber layer boundary B2, the interface between inner and outer segments of the photoreceptors B5, the inner boundary of the retinal pigment epithelium B6, and the retinal blood vessel area V) acquired in step S410.

<Step S620>

In step S620, the parameter setting unit 1421 performs various parameter settings based on the distribution of the eye part features acquired in step S410. More specifically, the parameter setting unit 1421 sets the following five parameters.

Figure 7:
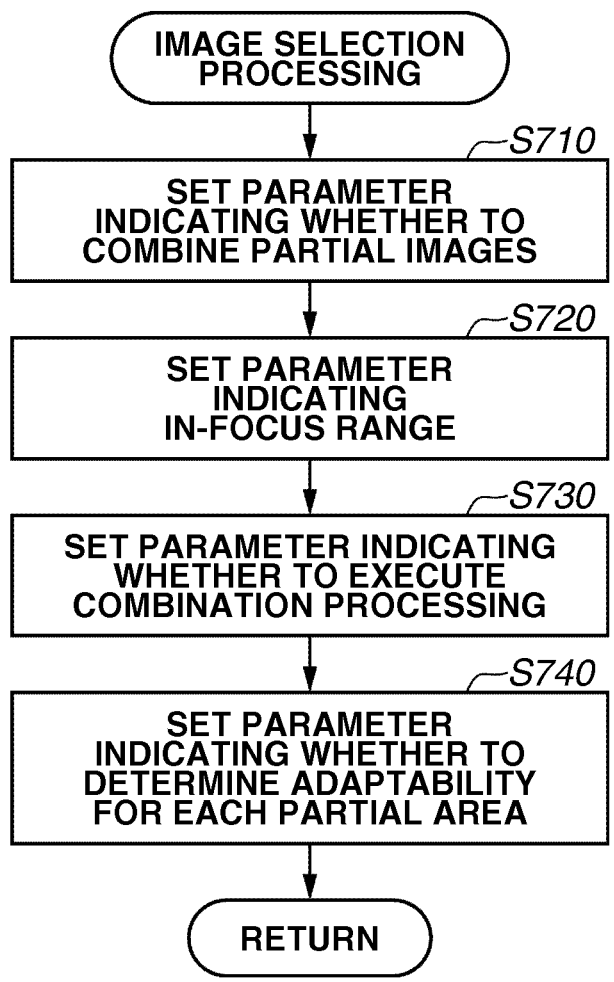
FIG. 7 is a flowchart illustrating an example of parameter setting processing that can be performed by a parameter setting unit.

(i) determination whether to combine a plurality of partial images or use a single SLO image (ii) range to identify in-focus state (iii) number of partial image candidates to be selected (iv) determination whether to execute combination processing if there is a plurality of partial image candidates (v) determination whether to set adaptability for each partial image FIG. 7 is a flowchart illustrating an example of the parameter setting processing.

In step S710, the parameter setting unit 1421 sets the parameter (i) indicating whether to combine a plurality of partial images. The parameter setting unit 1421 performs setting of the parameter (i) with reference to a deformation degree of an observation target relative to a normal structure.

In the present exemplary embodiment, if it is determined that the observation target (i.e., the interface between inner and outer segments of the photoreceptors) is deformed greatly as illustrated in FIG. 5B, the image processing apparatus selects partial images different in focus position at each position (x, y) of the imaging range. On the other hand, if it is determined that the observation target (i.e., the interface between inner and outer segments of the photoreceptors) is a normal eye and is not deformed so much as illustrated in FIG. 5A, the image processing apparatus select partial images at predetermined focus positions.

For example, to determine a bending degree of a layer shape, the parameter setting unit 1421 sets a plurality of control points on a layer boundary and determines that the layer shape includes an abnormal portion if an angle formed between a line segment connecting an arbitrary control point to a neighboring control point and another line segment connecting the arbitrary control point to the other neighboring control point is less than a predetermined value.

In step S720, the parameter setting unit 1421 sets the parameter (ii) indicating an in-focus range. More specifically, the parameter (ii) represents the distance from the photoreceptor cell layer boundary. If the parameter (ii) is less than a predetermined threshold, it is determined as being in focused state. Further, the deviation of the focus position relative to the interface between inner and outer segments of the photoreceptors in the optical axis direction within the above-described threshold range indicates a focus matching degree. SLO images whose focus position center is set to be less than the parameter (ii) in distance from the interface between inner and outer segments of the photoreceptors are selected as partial images.

The parameter setting unit 1421 performs the above-described determination for each partial area (for each pixel in the present exemplary embodiment). In the present exemplary embodiment, the parameter setting unit 1421 sets the parameter (ii) to be 50 μm. Further, the parameter setting unit 1421 determines the parameter (iii) indicating the number of partial image candidates to be selected based on the parameter (ii) indicating the in-focus range and the focus position interval of the SLO image group.

In the present exemplary embodiment, a concerned point is regarded as being present in an in-focus range if the distance from the interface between inner and outer segments of the photoreceptors is within 50 μm in the up-and-down direction. The focus position changes at intervals of 20 μm to acquire the SLO image group. Therefore, the number of the partial image candidates is five at most.

If the interface between inner and outer segments of the photoreceptors is positioned around the center (e.g., F5) of the focus positions F1 to F10 of the SLO image group, a relatively large number of SLO images can be selected as partial image candidates. On the other hand, if the interface between inner and outer segments of the photoreceptors is positioned around the focus position F1 or F10, the number of SLO images selected as partial image candidates is small.

In step S730, the parameter setting unit 1421 sets the parameter (iv) indicating whether to execute combination processing. The parameter (iv) is the parameter indicating whether to execute the combination processing if there is a plurality of partial image candidates. In the present exemplary embodiment, a user can input an instruction beforehand via the instruction acquisition unit 150 to set the parameter. However, any other method is employable to determine whether to execute the combination processing. For example, it is useful to perform the determination automatically based on an appropriate index (e.g., average S/N ratio of partial images).

The above-described parameter is set entirely for the selected SLO image group.

In step S740, the parameter setting unit 1421 sets the parameter (v) indicating whether to determine the adaptability for each partial area. If there is a plurality of partial image candidates, the parameter setting unit 1421 determines the adaptability for each partial image to select a most suitable candidate and then determines the adaptability for a combination of partial images or simply determines the adaptability for a combination of partial images, according to the parameter (v) having been set in step S740.

In the present exemplary embodiment, a user can input an instruction beforehand via the instruction acquisition unit 150 to set the parameter. However, as another example, it is useful to perform the determination automatically based on a value indicating the sharpness or contrast of an image. In the present exemplary embodiment, the size of a partial image is equal to one pixel. Therefore, the parameter setting unit 1421 does not perform the adaptability determination processing for each partial image. If the size of a partial image is greater than one pixel, the parameter setting unit 1421 can set the parameter (v).

<Step S625>

In step S625, the selection unit 142 determines whether the structure includes any abnormal portion based on the parameter (i) having been set in step S710. If it is determined that the structure includes an abnormal portion (YES in step S625), the processing proceeds to step S630. If it is determined that the structure does not include any abnormal portion (NO in step S625), the processing proceeds to step S660.

<Step S630>

In step S630, to set the focus position to be adjacent to the observation target (i.e., the interface between inner and outer segments of the photoreceptors) at each position on the eye-ground, the partial image candidate selection unit 1422 selects partial images whose focus positions are adjusted to be adjacent to the bent interface between inner and outer segments of the photoreceptors. As having being obtained for the parameters (ii) and (iii) in step S620, the partial image candidate selection unit 1422 selects partial images as partial image candidates because the distance from the interface between inner and outer segments of the photoreceptors is less than 50 μm. The partial image candidate selection unit 1422 performs the above-described processing for each SLO image on the pixel-by-pixel basis.

<Step S635>

In step S635, the selection unit 142 determines whether to perform the processing for combining the partial images selected based on the parameter (iv) having been set in step S730. If the selection unit 142 performs the combination processing (YES in step S635), the processing proceeds to step S640. If the selection unit 142 does not perform the combination processing (NO in step S635), the processing proceeds to step S650.

<Step S640>

In step S640, the integration unit 1423 performs the combination processing using the partial image candidates selected in step S630 based on the parameter (iv) having been set in step S730. To reduce the influence of the involuntary eye movement during fixation, the integration unit 1423 performs positioning processing on each partial image candidate in the same manner as the processing performed in step S430. The integration unit 1423 excludes a partial image from the partial image candidates to be combined if the partial image has a positioning parameter whose value is equal to or greater than a predetermined value.

For example, if there are five partial images (p1 through p5) that are determined as being in focused state, the integration unit 1423 performs positioning of these partial images and obtains a single partial image with reference to an average pixel value of corresponding pixels.

<Step S650>

The partial image adaptability determination unit 1424 calculates an adaptability value indicating whether the partial image selected with reference to image features of the partial image candidates is an appropriate image. In the present exemplary embodiment, the partial image adaptability determination unit 1424 uses a value indicating the contrast of the partial image as the adaptability value. If the calculated adaptability value is equal to or greater than a predetermined threshold, the partial image adaptability determination unit 1424 recognizes the selected partial image as an adaptable partial image.

The index representing the adaptability is not limited to the above-described value. For example, an arbitrary known image quality evaluation index or an image feature quantity is employable as the adaptability value. In the present exemplary embodiment, the partial image adaptability determination unit 1424 does not perform the above-described processing because the size of the partial image is equal to one pixel.

<Step S655>

If the adaptability is less than the threshold, the partial image adaptability determination unit 1424 recognizes the selected partial image as an inadaptable partial image. In this case, the processing returns to step S630 to change the eye part feature parameters and repeat the processing in step S630 and subsequent steps until it is determined that the selected partial image is adaptable.

If the adaptability exceeds the threshold, the partial image adaptability determination unit 1424 recognizes the selected partial image as an adaptable partial image and terminates the processing of step S440. In the present exemplary embodiment, the partial image adaptability determination unit 1424 automatically terminates the processing of step S440 because the size of the partial image is equal to one pixel.

<Step S660>

If it is determined that the structure does not include any abnormal portion (NO in step S625), the selection unit 142 selects an SLO image whose focus position is closest to the interface between inner and outer segments of the photoreceptors. As another example, the parameter (ii) indicating the in-focus range having been set in step S720 can be used to select SLO images to be combined.

Figure 8:
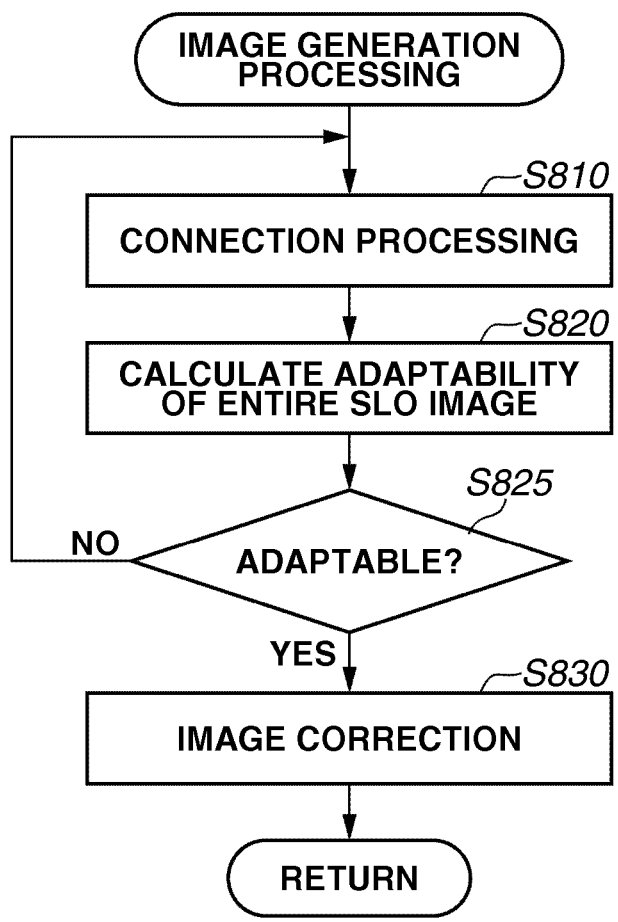
FIG. 8 is a flowchart illustrating an example of image generation processing that can be performed by an image generation unit.

Next, the processing to be executed in step S450 is described in detail below with reference to FIG. 8.

<Step S810>

In step S810, the connection unit 1431 generates an SLO image candidate by connecting the partial images corresponding to respective positions on the eyeground, which have been selected in step S650, along a plane extending in the x and y directions.

As described above, in a case where the processing skips step S640 or step S650 and directly proceeds to step S810, the connection unit 1431 selects a predetermined combination of partial images, among respective eyegrounds, and connects the selected partial images along the plane extending in the x and y directions.

<Step S820>

The SLO image adaptability determination unit 1432 calculates an index value indicating whether the image generated in step S810 is adaptable to the observation (analysis). In the present exemplary embodiment, the SLO image adaptability determination unit 1432 measures the S/N ratio and the sharpness of respective partial images to determine the degree of dispersion in observation (analysis) conditions between the partial images.

If both values satisfy the condition that a sum of square errors of respective partial images is less than a predetermined value, the SLO image adaptability determination unit 1432 determines that the image generated in step S810 is adaptable. The processing proceeds to step S830. On the contrary, if at least one of the measured values is equal to or greater than a predetermined value, the SLO image adaptability determination unit 1432 determines that the image generated in step S810 is inadaptable. In this case, the processing returns to step S810. The SLO image adaptability determination unit 1432 changes the combination of partial image candidates and performs the above-described processing in step S820 again until the adaptability is confirmed.

<Step 830>

In step S830, the correction unit 1433 calculates a change amount in pixel value and smoothness in edge shape at a boundary area of each selected partial area of the SLO images selected in step S820. In the present exemplary embodiment, dispersion values obtainable by performing arbitrary known edge detection processing with respect to the angle between edge forming control points are usable as the change amount in pixel value in the direction perpendicular to the boundary area, and the smoothness in edge shape. If the change amount in density or shape is equal to or greater than a predetermined value, the correction unit 1433 performs luminance adjustment for the boundary area.

Thus, even when the shape of a photoreceptor cell layer is deformed greatly, the correction unit 1433 can obtain an image easy to observe or analyze the photoreceptor cell in the imaging range.

According to the above-described configuration, the image processing apparatus 10 selects a group of SLO partial images whose focus positions are set to be adjacent to the photoreceptor cell layer boundary at each position of the eyeground having a greatly deformed photoreceptor cell layer due to aged macular degeneration and generates a new SLO image by combining and integrating the selected SLO partial images.

Thus, even in a case where the shape of a target photoreceptor cell layer is deformed greatly, users can easily observe or analyze the photoreceptor cell in the imaging range. Further, the image processing apparatus 10 calculates an index value indicating the degree of deformation in the photoreceptor cell layer. If the degree of the deformation is not large, the image processing apparatus 10 selects an SLO image that is in most focused state. Thus, users can easily observe the structure of the observation target.

As described above, the image processing apparatus according to the first exemplary embodiment generates a new SLO image based on SLO images read out of a storage apparatus.

On the other hand, an image processing apparatus according to a second exemplary embodiment acquires SLO images directly from an eye part imaging apparatus (i.e., a composite apparatus 200 including an adaptive optics SLO and an OCT) and performs image generation processing as described below. Further, in the present exemplary embodiment, an observation (analysis) target is a nerve fiber bundle of an optic disc area in cases of myopic glaucoma.

More specifically, the composite apparatus 200 includes an SLO apparatus capable of acquiring a planar image by correcting an optical aberration of an eye to be tested with a spatial optical modulator and a Fourier domain OCT apparatus capable of acquiring a tomographic image. The image processing apparatus according to the second exemplary embodiment can directly acquire SLO images and OCT volume images from the composite apparatus 200.

Further, the image processing apparatus according to the second exemplary embodiment selects partial images whose focus positions are set to be adjacent a retinal inner layer boundary at each position on the eyeground from SLO images captured at various focus positions, based on information indicating a retinal inner layer boundary acquired from the OCT volume image. Then, the image processing apparatus according to the second exemplary embodiment generates a new SLO image by connecting and integrating the selected partial images.

Thus, even when the shape of the inner limiting membrane or the retinal inner layer boundary is deformed greatly due to myopia and glaucoma, an operator can easily observe or analyze the distribution of the nerve fiber bundle in the imaging range.

An example configuration of the image processing apparatus according to the second exemplary embodiment is described in detail below, although the descriptions of components or portions similar to those described in the first exemplary embodiment are excluded.

Figure 9:
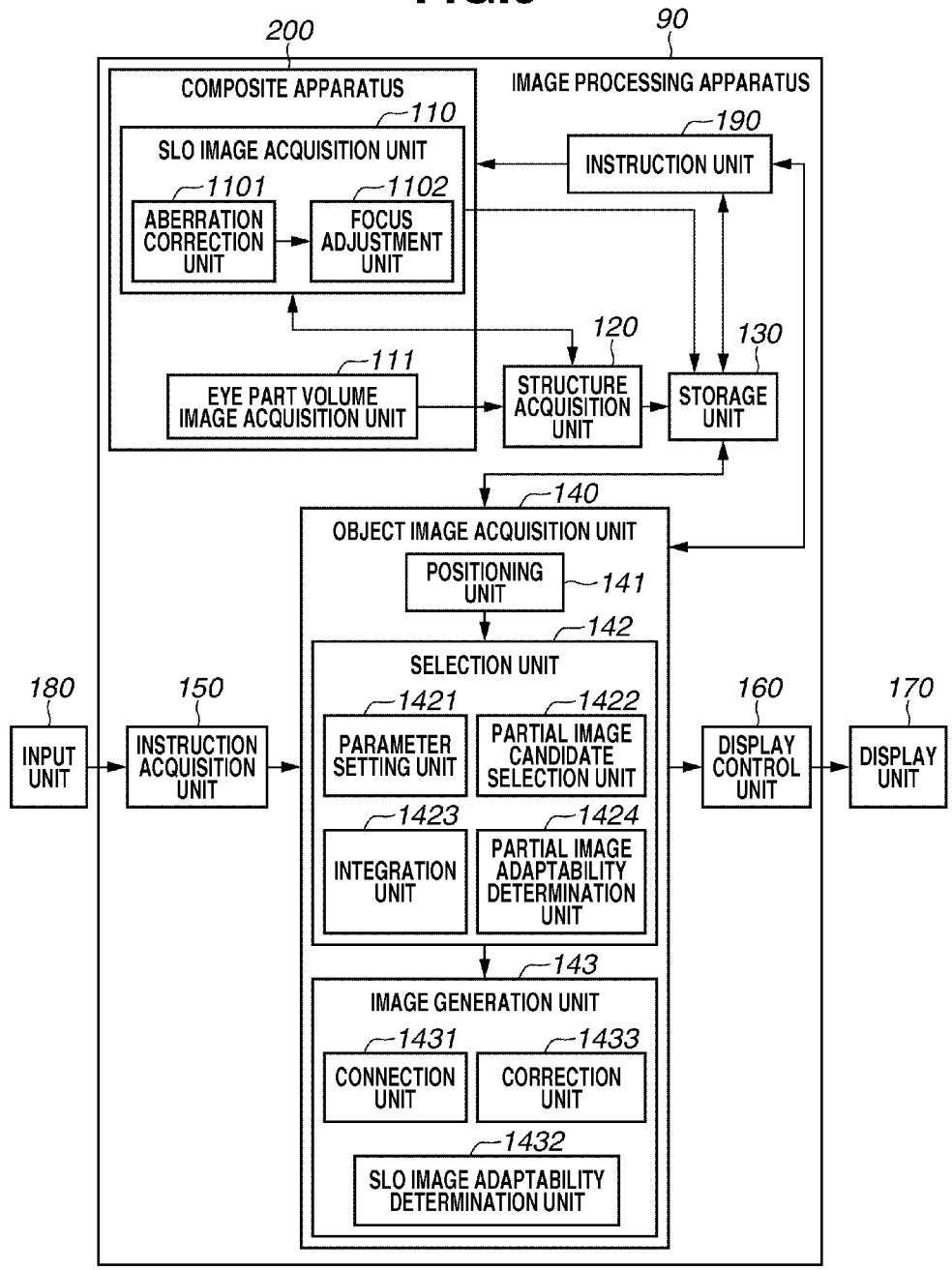
FIG. 9 illustrates an example configuration of the image processing apparatus according to a second exemplary embodiment.

FIG. 9 illustrates a functional block diagram illustrating an image processing apparatus 90 according to the present exemplary embodiment. The image processing apparatus 90 includes the composite apparatus 200 that is composed of the SLO image acquisition unit 110 and an eye part volume image acquisition unit 111.

The second exemplary embodiment is different from the first exemplary embodiment in that the structure acquisition unit 120 acquires eye part features directly from an eye part volume image captured by the eye part volume image acquisition unit 111. Further, the second exemplary embodiment is different from the first exemplary embodiment in that the SLO image acquisition unit 110 includes an aberration correction unit 1101 and a focus adjustment unit 1102 to capture SLO images.

Further, the image processing apparatus 90 includes an instruction unit 190 that can instruct the SLO image acquisition unit 110 to perform a shooting operation. The instruction unit 190 generates a shooting instruction based on an image obtained by the object image acquisition unit 140. Further, the instruction unit 190 is functionally operable as a setting (or correction) unit that can set (or correct) shooting conditions (e.g., focus position, focus interval, etc.). In this respect, the image processing apparatus 90 is functionally operable as a shooting control apparatus (i.e., a shooting instruction apparatus) or an imaging apparatus.

Figure 10:
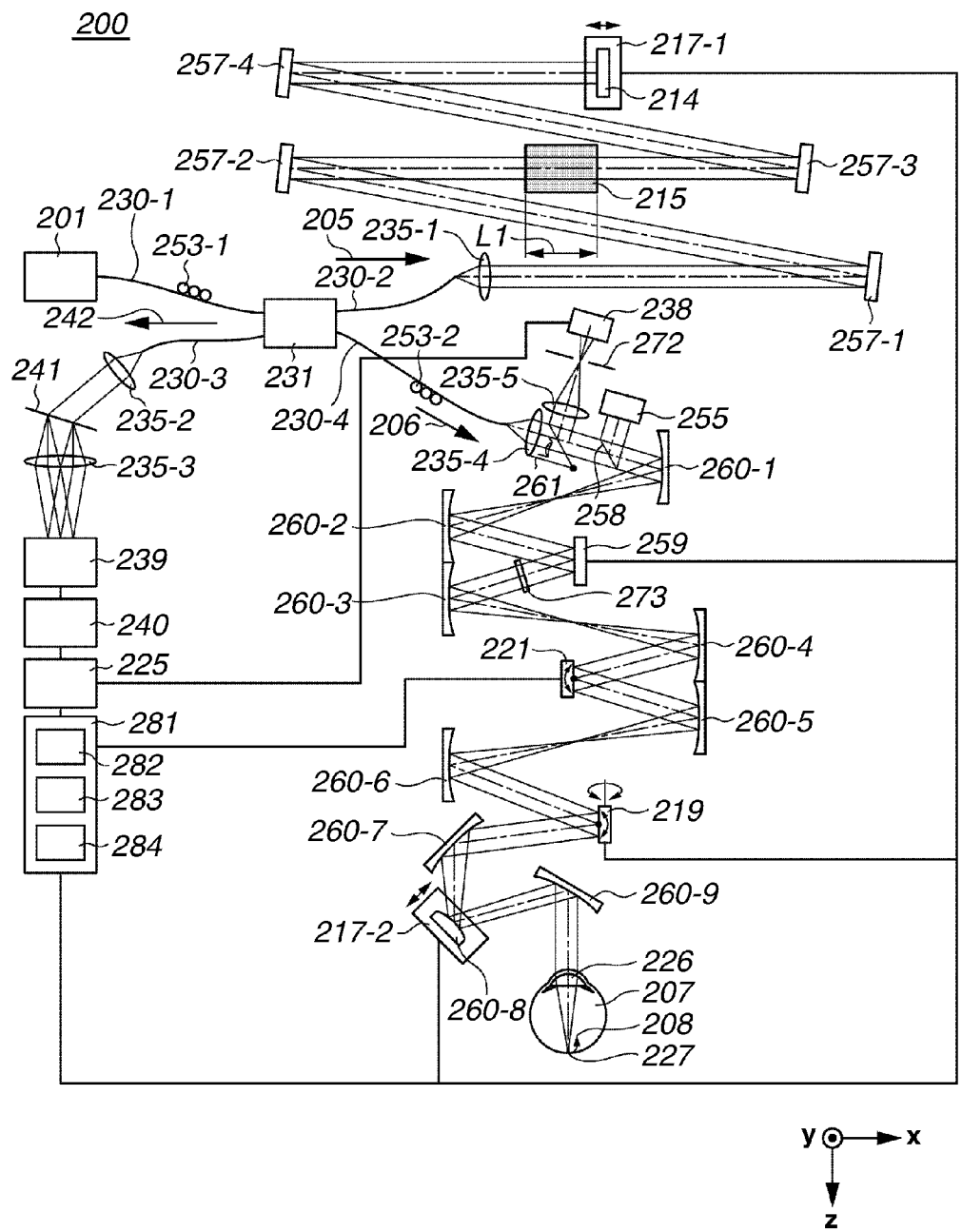
FIG. 10 illustrates a hardware configuration of a composite apparatus according to the second exemplary embodiment.

FIG. 10 illustrates a schematic configuration of the composite apparatus 200.

<Overall Configuration>

An optical coupler 231 can split light, if it is emitted from a light source 201, into a reference beam 205 and a measuring beam 206. The composite apparatus 200 can guide the measuring beam 206 to an eye to be tested 207 (i.e., an observation target) via a single-mode fiber 230-4, a spatial optical modulator 259, an XY scanner 219, an X scanner 221, and a plurality of spherical mirrors 260-1 to 260-9.

The measuring beam 206 is reflected or scattered when it reaches the eye to be tested 207 and travels as an optical feedback 208 toward a detector 238 or a line sensor 239.

The detector 238 can convert the light intensity of the optical feedback 208 into a voltage signal. The detector 238 can form a planar image of the eye to be tested 207 based on the obtained voltage signal. Further, the detector 238 can calculate blood flow velocity based on the acquired plurality of planar images. Further, the line sensor 239 can mix the received reference beam 205 and the optical feedback 208 to form a tomographic image of the eye to be tested 207. Further, the line sensor 239 can extract a three-dimensional flow path of a blood vessel based on a plurality of acquired tomographic images.

The spatial optical modulator 259 according to the present exemplary embodiment is a device having the capability of correcting a wavefront aberration. However, a mirror having a variable shape is usable if it can correct the wavefront aberration.

<Light Source>

The light source 201 is a super luminescent diode (SLD) that can serve as a low-coherent light source. The light source 201 can emit light having a wavelength of 830 nm and a bandwidth of 50 nm. The low-coherent light source according to the present exemplary embodiment is useful to acquire a planar image having a smaller speckle noise component. Further, the type of the light source is not limited to the SLD and can be any other type, such as amplified spontaneous emission (ASE), if it can emit low-coherent light.

Further, when a target to be measured is an eye, it is desired that the wavelength is in the near infrared ray range. Further, it is desired that the wavelength is sufficiently short (830 nm in the present exemplary embodiment) because the wavelength influences the horizontal resolution of an obtained planar image. The wavelength to be selected for the light source 101 is variable depending on an observation target to be measured. Further, the SLD (i.e., the low-coherent light source) is suitable to capture a tomographic image.

<Reference Optical Path>

The reference beam 205 travels along the following optical path. The reference beam 205 split by the optical coupler 231 can reach a lens 235-1 via a single-mode fiber 230-2. The reference beam 205, after passing through the lens 235-1, travels as a parallel beam having a beam diameter of 4 mm.

Then, after being reflected by the mirrors 257-1 to 257-4, the reference beam 205 can reach a mirror 214 (i.e., a reference mirror). The optical length of the reference beam 205 is set to be substantially equal to the optical path length of the measuring beam 206. Therefore, the reference beam 205 and the measuring beam 206 can interfere with each other.

Then, after being reflected by the mirror 214, the reference beam 205 returns to the optical coupler 231. In the present exemplary embodiment, the reference beam 205 passes through a dispersion compensation glass 215, which can compensate a dispersion component for the reference beam 205 when the measuring beam 206 travels toward and returns from the eye to be tested 207. In the present exemplary embodiment, the diameter of an eyeball is set to be a representative value for Japanese (more specifically, L1=23 mm).

Further, an electric stage 217-1 can move in a direction indicated by an arrow to adjust (control) the optical path length of the reference beam 205. To this end, a personal computer 225 controls an electric stage driver 283 provided in a driver unit 281 to drive the electric stage 217-1.

<Measurement Optical Path>

The measuring beam 206 travels along the following optical path.

The measuring beam 206 split by the optical coupler 231 can reach a lens 235-4 via the single-mode fiber 230-4. The measuring beam 206, after passing through the lens 235-4, travels as a parallel beam having a beam diameter of 4 mm. Further, a polarizing controller 253-1 or 253-2 can adjust a polarizing state of the measuring beam 206. In the present exemplary embodiment, the polarizing controller 253-1 or 253-2 adjusts the polarizing state of the measuring beam 206 to be linearly polarized in a direction parallel to the drawing surface.

The measuring beam 206 passes through a beam splitter 258 and a movable beam splitter 261 and reaches the spatial optical modulator 259 via the spherical mirrors 260-1 and 260-2 to be modulated. In the present exemplary embodiment, the spatial optical modulator 259 is a modulator that utilizes the orientation characteristics of a liquid crystal to modulate the measuring beam 206. More specifically, the spatial optical modulator 259 is disposed in a predetermined direction where the spatial optical modulator 259 can modulate the phase of linear polarization parallel to the drawing surface (i.e., the P polarization).

Further, the measuring beam 206 passes through a polarizing plate 273 and reaches a mirror of the X scanner 221 via spherical mirrors 260-3 and 260-4. In the present exemplary embodiment, the polarizing plate 273 has a role of guiding only the linear polarization parallel to the drawing surface, of the optical feedback 208, to the spatial optical modulator 259.

Further, in the present exemplary embodiment, the X scanner 221 is an X scanner that performs scanning with the measuring beam 206 in a direction parallel to the drawing surface. For example, the X scanner 221 is a resonance scanner having a drive frequency of approximately 7.9 kHz.

Further, the measuring beam 206 reaches a mirror of the XY scanner 219 via the spherical mirrors 260-5 and 260-6. In the present exemplary embodiment, the XY scanner 219 has only one mirror. However, in an actual arrangement, two mirrors are disposed adjacently as an X scanning mirror and a Y scanning mirror. Further, the center of the measuring beam 206 coincides with a rotational center of the mirror provided in the XY scanner 219. The drive frequency of the XY scanner 219 is variable in the range 0 to 500 Hz.

The spherical mirrors 260-7 to 260-9 can constitute an optical system that can perform scanning on a retina 227. The optical system has a role of scanning the retina 227 with the measuring beam 206 around a fulcrum positioned in the vicinity of a cornea 226.

In the present exemplary embodiment, the measuring beam 206 has a beam diameter of 4 mm. However, the beam diameter of the measuring beam 206 may be larger enough to acquire a high-resolution tomographic image.

Further, an electric stage 217-2 can move in a direction indicated by an arrow to adjust (control) the position of the spherical mirror 260-8 (i.e., an associated spherical mirror). Similar to the electric stage 217-1, the electric stage 217-2 can be controlled by the electric stage driver 283.

When the position of the spherical mirror 260-8 is adjusted, the measuring beam 206 can be focused on a predetermined layer of the retina 227 of the eye to be tested 207 and can be visually recognized. The position of the spherical mirror 260-8 is initially adjusted to let the measuring beam 206 travel as a parallel beam and reach the cornea 226. Further, for example, if the eye to be tested 207 has refraction abnormality, it is useful to adjust the position of the spherical mirror 260-8.

The measuring beam 206 reflects and scatters on the retina 227 when the measuring beam 206 reaches the eye to be tested 207 and travels as the optical feedback 208 toward the optical coupler 231 again, and reaches the line sensor 239.

Further, after being reflected by the movable beam splitter 261, a part of the optical feedback 208 reaches the detector 238 via a lens 235-5. In the present exemplary embodiment, a light shielding plate 272 with a pinhole has a role of blocking unnecessary light (i.e., a light component that has not focused at the retina 227) of the optical feedback 208.

Further, the light shielding plate 272 is disposed at a position conjugate with the in-focus position of the lens 235-5. The pinhole of the light shielding plate 272 has a diameter of, for example, 50 μm. The detector 238 is, for example, a high-speed and high-sensitive optical sensor, such as Avalanche Photo Diode (APD).

Further, a part of the optical feedback 108 split by the beam splitter 258 reaches a wavefront sensor 255. The wavefront sensor 255 is a Shack-Hartmann wavefront sensor. In the present exemplary embodiment, the spherical mirrors 260-1 to 260-9 are disposed in such a way that the XY scanner 219, the X scanner 221, the cornea 226, the wavefront sensor 255, and the spatial optical modulator 259 are optically conjugate with each other.

The wavefront sensor 255 and the spatial optical modulator 259 cooperatively constitute an adaptive optics system. The wavefront sensor 255 can measure the aberration of the eye to be tested 207. Further, the spatial optical modulator 259 can correct the aberration of the eye to be tested 207. Further, when the personal computer 225 performs real-time control for the spatial optical modulator 259 based on the obtained aberration, the aberration generated by the eye to be tested 207 can be corrected and a tomographic image having excellent horizontal resolution can be acquired.

<Configuration of Measuring System>

Next, an example configuration of the measuring system is described below. The composite apparatus 200 can acquire tomographic images (OCT images) and planar images (SLO images).

First, a tomographic image measuring system has the following features. The optical coupler 231 combines the optical feedback 208 with the reference beam 205. Mixed light 242 reaches a transmission grating 241 via a single-mode fiber 230-3 and a lens 235-2. After being dispersed for each wavelength by transmission grating 241, the mixed light 242 finally reaches the line sensor 239 via a lens 235-3.

The line sensor 239 converts the light intensity into a voltage signal for each position (wavelength). A frame grabber 240 converts the voltage signal into a digital value. The personal computer 225 forms a tomographic image of the eye to be tested 207. In the present exemplary embodiment, the line sensor 239 includes 1,024 pixels and can obtain the intensity of the mixed light 242 for each wavelength (each of 1,024 subsections).

A planar image (SLO image) measuring system has the following features. The movable beam splitter 261 reflects a part of the optical feedback 208. The light shielding plate 272 blocks an unnecessary light component of the reflected light. Then, the light reaches the detector 238. The detector 238 converts the intensity of the light into an electric signal. The personal computer 225 performs data processing on the obtained electric signal in synchronization with scanning signals of the X scanner 221 and the XY scanner 219 and forms a planar image.

A part of the optical feedback 208 split by the beam splitter 258 reaches the wavefront sensor 255. The wavefront sensor 255 measures an aberration of the optical feedback 208. The personal computer 225 receives an image signal obtained by the wavefront sensor 255 and calculates an aberration value. The obtained aberration (i.e., the aberration of the eye to be tested 207) can be expressed using Zernike polynomials. The Zernike polynomial expression includes a tilt term, a defocus term, an astigmatism term, a coma term, and a trifoil term.

<OCT Image Acquisition Method>

An example tomographic image (i.e., OCT image) acquisition method that can be realized by the composite apparatus 200 is described in detail below with reference to FIGS. 11A to 11C. The composite apparatus 200 controls the XY scanner 219 and causes the X scanner 221 to serve as a stationary mirror, while the line sensor 239 acquires interference fringes to acquire a tomographic image of the retina 227.

Further, the composite apparatus 200 controls the movable beam splitter 261 to prevent the optical feedback 208 from reaching the detector 238. Further, the personal computer 225 controls an optical scanner driver 282 provided in the driver unit 281 to drive the X scanner 221 and the XY scanner 219. An example method for acquiring a tomographic image (i.e., an image on a plane parallel to the optical axis) of the retina 227 is described below.

Figure 11A:
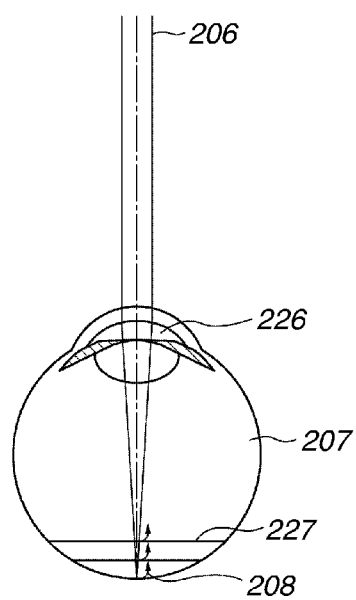

FIG. 11A schematically illustrates the eye to be tested 207, which can be observed by the composite apparatus 200. As illustrated in FIG. 11A, the measuring beam 206 reaches the retina 227 after passing through the cornea 226 and is reflected and scattered at various positions, and then travels as the optical feedback 208 and reaches the line sensor 239 with time delay that depends on each position.

In the present exemplary embodiment, the light source 201 has a wide bandwidth and a short coherence length. Therefore, if the length of the reference optical path is substantially equal to the length of the measurement optical path, the line sensor 239 can detect interference fringes caused by the light passing through respective layers of the retina and the light traveling via the reference mirror. As described above, the line sensor 239 can acquire interference fringes in a spectral area on the wavelength axis.

Next, the composite apparatus 200 converts the interference fringes (i.e., information obtained from the wavelength axis) into interference fringes on an optical frequency axis considering characteristics of the line sensor 239 and the transmission grating 241. Further, the composite apparatus 200 obtains information in the depth direction by applying inverse Fourier transform to the converted interference fringes on the optical frequency axis.

Figure 11B:
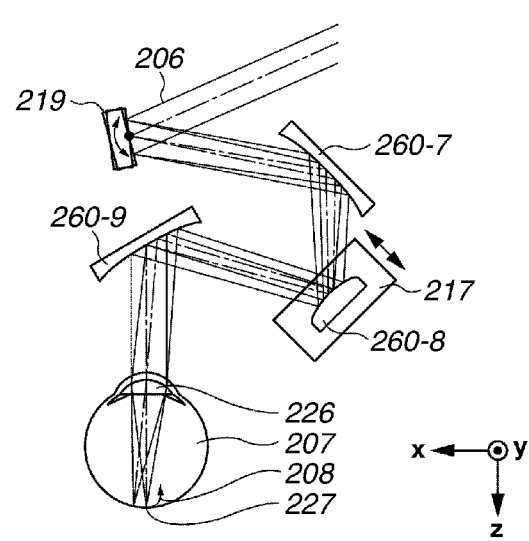

Further, as illustrated in FIG. 11B, the composite apparatus 200 can detect (obtain) interference fringes for each position along the X axis while driving the XY scanner 219. More specifically, the composite apparatus 200 can obtain the information in the depth direction at each position along the X axis.

As a result, the composite apparatus 200 can obtain a two-dimensional intensity distribution of the optical feedback 208 on the XZ plane. More specifically, the composite apparatus 200 can form a tomographic image 232 (see FIG. 11C). In general, the tomographic image 232 is composed of arrayed intensity components of the optical feedback 208 as described above. For example, the composite apparatus 200 can display the tomographic image 232 by applying the gray scale to the intensity components. The length of the tomographic image 232 in the X direction is 700 μm.

Figure 11C:
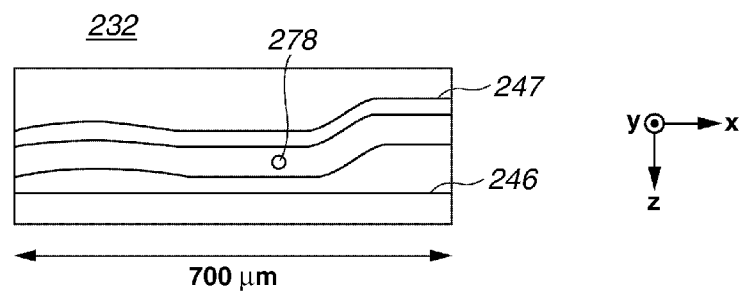

The tomographic image 232 illustrated in FIG. 11C includes highlighted boundary lines that represent a pigmented layer of a retina 246 and an optic layer 247. The tomographic image 232 further includes a blood vessel 278. Further, the composite apparatus 200 can depict a three-dimensional flow path of the blood vessel by acquiring a plurality of tomographic images at numerous positions along the Y axis.

<SLO Image Acquisition Method>

Next, an example planar image (SLO image) acquisition method that can be realized by the composite apparatus 200 is described below.

The composite apparatus 200 controls the XY scanner 219 only in the Y-axis direction and also controls the X scanner 221, while preventing the XY scanner 219 from moving in the X axis. The composite apparatus 200 acquires a planar image of the retina 227 based on intensity values of the optical feedback 208 detected by the detector 238. The personal computer 225 can control the optical scanner driver 282 of the driver unit 281 to drive the X scanner 221 and the XY scanner 219.

Further, the composite apparatus 200 can control the spatial optical modulator 259 based on an aberration of the eye to be tested 207 measured by the wavefront sensor 255. The composite apparatus 200 can acquire planar images while correcting aberration generated by the eye to be tested 207. Further, the composite apparatus 200 can acquire planar images by performing real-time control for the spatial optical modulator 259.

In the present exemplary embodiment, the composite apparatus 200 adjusts the focus position to acquire an SLO image by moving the spherical mirror 260-8 in the direction indicated by an arrow as illustrated in FIG. 11B. More specifically, the composite apparatus 200 moves the spherical mirror 260-8 in such a way as to maximize the luminance at the outer boundary of the retinal pigment epithelium B6. Thus, the composite apparatus 200 can set the focus position on the boundary B6.

Then, the composite apparatus 200 can adjust the focus position on a different position by further moving the spherical mirror 260-8 by a predetermined amount. For example, it is desired to design the apparatus in such a way as to realize shifting of 5 μm in focus position in response to 1 mm movement of the spherical mirror 260-8. However, any other focus adjustment method is employable. For example, the spatial optical modulator 259 can be used to adjust the focus position.

Further, a mirror having a variable shape is usable to perform aberration correction or to perform focus adjustment. Moreover, it is useful to constitute the optical system by a refraction optical system using a lens instead of the spherical mirror to perform the adjustment by moving a focus lens.

Figure 12:
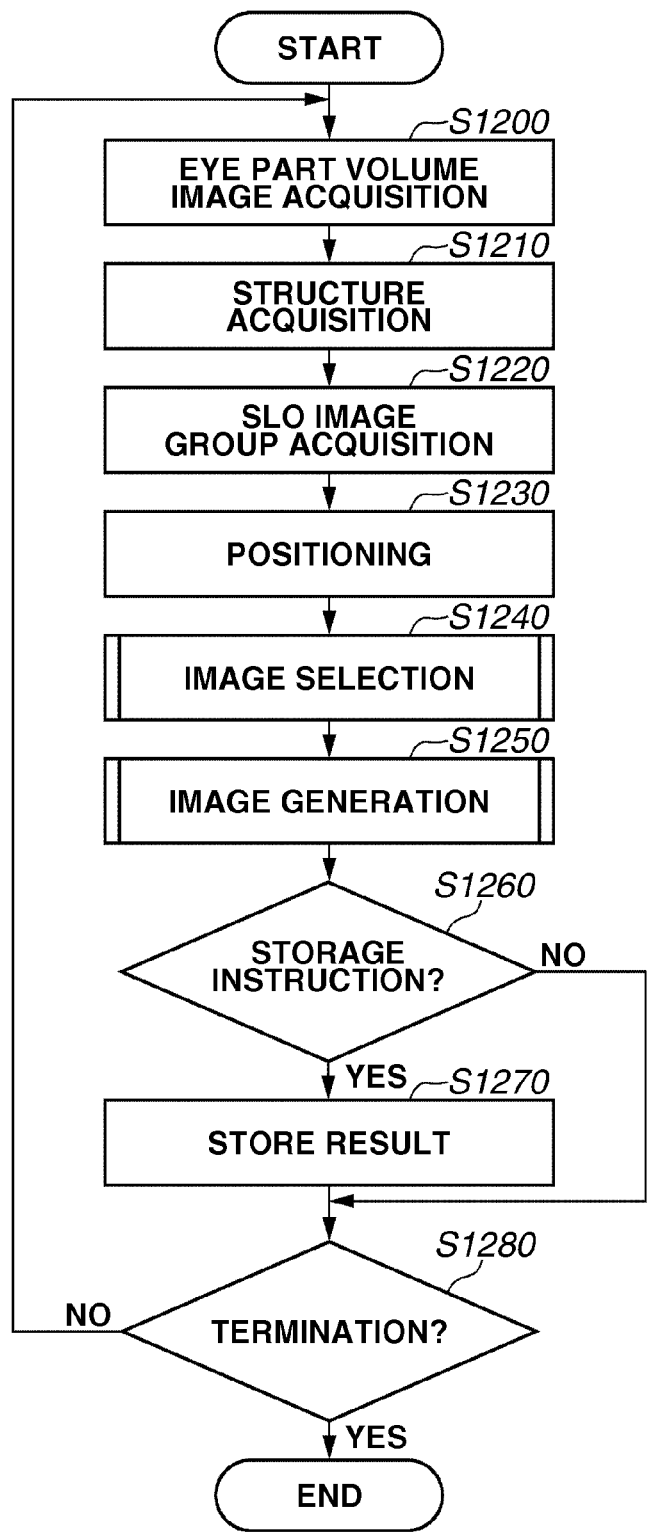
FIG. 12 is a flowchart illustrating example processing that can be performed by the image processing apparatus according to the second exemplary embodiment.

FIG. 12 illustrates an example of the image generation processing according to the present exemplary embodiment. Processing to be performed in step S1230, step S1250, step S1260, and step S1270 is similar to the processing in step S430, step S450, and step S470 described in the first exemplary embodiment, and accordingly its description is omitted. Processing to be performed in step S1200, step S1210, step S1220, step S1240, and step S1280 according to the present exemplary embodiment is described in detail below.

<Step S1200>

Figure 13A:
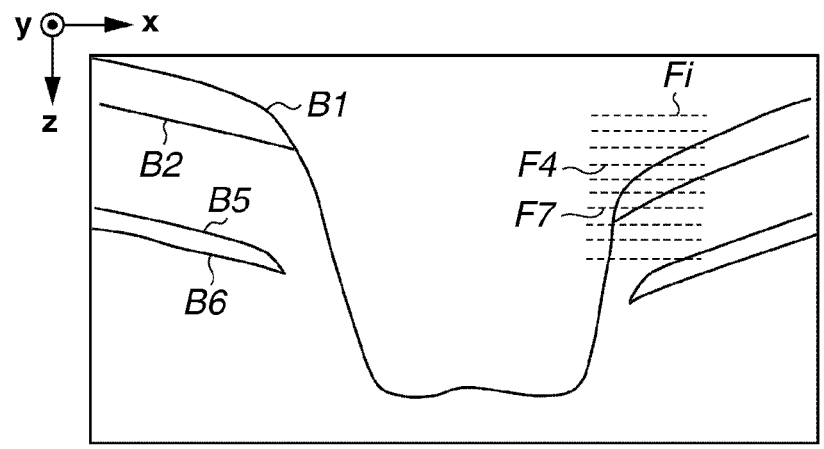

The eye part volume image acquisition unit 111 captures an eye part volume image and transmits the eye part volume image to the structure acquisition unit 120. The eye part volume image acquired in the present exemplary embodiment includes an optic disc area as illustrated in FIG. 13A, in which the inner limiting membrane and the retinal inner layer boundary are deformed due to myopia and glaucoma.

<Step S1210>

The structure acquisition unit 120 acquires eye part features from the eye part volume image acquired by the eye part volume image acquisition unit 111. In the present exemplary embodiment, it is presumed that an observation (or analysis) target instructed beforehand by the instruction acquisition unit 150 is the nerve fiber bundle.

The eye part features extracted by the structure acquisition unit 120 include the inner limiting membrane B1, the nerve fiber layer boundary B2, the inner plexiform layer boundary (not illustrated), the interface between inner and outer segments of the photoreceptors B5, the outer boundary of the retinal pigment epithelium B6, and the retinal blood vessel (not illustrated). The structure acquisition unit 120 can use a layer boundary and retinal blood vessel extraction method that is similar to the method described in the first exemplary embodiment (see step S410).

<Step S1220>

The SLO image acquisition unit 110 adjusts the focus position based on the layer boundaries acquired by the structure acquisition unit 120 in step S1210 and captures a group of aberration corrected SLO images. In the present exemplary embodiment, the SLO image acquisition unit 110 sets a variation range Fi with respect to the focus position center based on a variation range of each of the inner limiting membrane B1 and the nerve fiber layer boundary B2 in the z coordinate (see FIG. 13A) and sets a variation interval of 20 μm.

<Step S1240>

Example processing to be performed by the selection unit 142 in step S1240 is described below in detail.

<Step S1280>

In step S1280, an observer observes an image displayed on the display unit 170 and, if there is any failure in the image (e.g., a problem in shooting position), the observer instructs restarting a shooting operation via the input unit 180. The image processing apparatus repeats the processing in step S1200 and subsequent steps. In this case, the instruction unit 190 instructs the composite apparatus 200 to perform a shooting operation again with reference to the input information (e.g., focus positions, interval of the focus positions, and the number of images to be captured). The composite apparatus 200 performs a shooting operation according to the instruction received from the instruction unit 190.

Further, in another example, if the object image acquisition unit 140 determines that an image quality index value of an image generated by the image generation unit 143 is less than a predetermined threshold, the instruction unit 190 sets the intervals of the focus positions to be smaller than the previous values so that the number of images to be captured can be increased. Alternatively, the instruction unit 190 can perform settings in such a way as to increase the number of SLO images to be captured at the same focus position so that a sufficient number of images can be obtained without changing the intervals of the focus positions.

Further, according to another example, the instruction unit 190 resets the shooting position if a sufficient number of images capturing the organization structure of an observation target cannot be obtained due to inappropriateness of the shooting position. For example, in a case where the number of partial candidates to be selected is five at most, if the object image acquisition unit 140 determines that the number of obtainable candidate images is less than a threshold because of deviation in the shooting position, the instruction unit 190 changes the setting of the shooting position. In this manner, it is feasible to reset shooting parameters based on previously captured images.

Figure 13B:
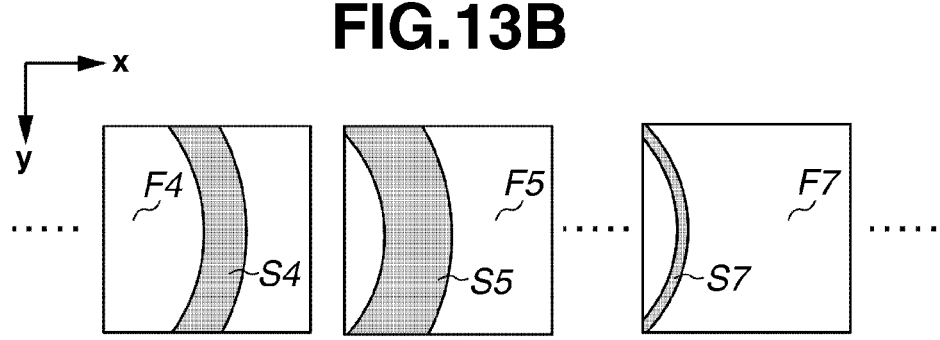
Figure 13C:
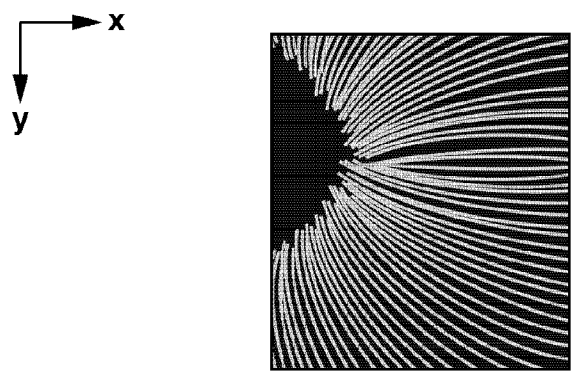

Example images that can be obtained through the above-described processing are described below with reference to FIGS. 13A to 13C. FIG. 13A illustrates an OCT tomographic image of an optic disc area captured by the composite apparatus 200, in which Fi (F1 through F10) indicates the imaging position of each SLO image. FIG. 13B illustrates a group of SLO images selected by the selection unit 142, in which each SLO image includes a partial area Si focused on the nerve fiber layer boundary B2 (i.e., the target to be captured). The image generation unit 143 combines these partial areas Si to obtain an integrated image of the nerve fiber bundle as illustrated in FIG. 13C.

The processing to be executed in step S1240 is described in detail below with reference to the flowchart illustrated in FIG. 6.

<Step S610>

The selection unit 142 acquires the eye part features (including the inner limiting membrane B1, the nerve fiber layer boundary B2, the interface between inner and outer segments of the photoreceptors B5, the inner boundary of the retinal pigment epithelium B6, and the retinal blood vessel area V) acquired in step S1210.

<Step S620>

The parameter setting unit 1421 sets the following parameters relating to SLO partial image selection method based on the distribution of the eye part features acquired in step S610.

(i) determination whether to combine a plurality of partial images or use a single SLO image (ii) parameter usable in partial image selection (iii) number of partial image candidates to be selected (iv) determination whether to execute combination processing if there is a plurality of partial image candidates (v) determination whether to set adaptability for each partial image With respect to the parameter (i), the image processing apparatus according to the present exemplary embodiment determines that the observation target (i.e., the nerve fiber layer boundary) is deformed greatly as illustrated in FIG. 13A. Therefore, the processing proceeds to step S630 to select partial images different in focus position at each position (x, y) in the imaging range.

A method for determining the degree of bending in layer shape used in the present exemplary embodiment is similar to the method described in the first exemplary embodiment, therefore its description is omitted. The size of a partial area is equal to 16 (=4×4) pixels. To satisfy the requirements of processing efficiency and accuracy at the same time, it is useful to set the size of each partial area to be smaller when the degree of deformation is larger. On the other hand, the size of each partial area can be set to be larger when the degree of deformation is smaller.

With respect to the parameter (ii), the image processing apparatus according to the present exemplary embodiment selects images whose focus position center is set to be less than a predetermined value in distance from the nerve fiber layer boundary as partial images. In the present exemplary embodiment, the parameter (ii) is set to be 30 μm as the distance from the nerve fiber layer boundary.

With respect to the parameter (iii), the image processing apparatus according to the present exemplary embodiment acquires a group of SLO images at a plurality of focus positions spaced at the intervals of 20 μm. Therefore, the number of partial image candidates is three.

With respect to the parameter (iv), the image processing apparatus determines whether to perform combination processing if there is a plurality of partial image candidates. In the present exemplary embodiment, the image processing apparatus performs the combination processing in response to an instruction input beforehand by a user via the instruction acquisition unit 150.

With respect to the parameter (v), the image processing apparatus determines an adaptability value based on an instruction having been input beforehand by a user via the instruction acquisition unit 150.

<Step S630>

To set the focus position to be adjacent to the observation target (i.e., the nerve fiber layer boundary) at each position on the eyeground, the partial image candidate selection unit 1422 selects partial images whose focus positions are adjusted to be adjacent to the bent nerve fiber layer boundary. As having being obtained for the parameters (ii) and (iii) in step S620, the partial image candidate selection unit 1422 selects three partial images as partial image candidates because the distance from the nerve fiber layer boundary is less than 30 μm.

<Step S640>

The integration unit 1423 performs combination processing using the partial image candidates selected in step S630, based on the determination result with respect to the parameter (iv) in step S620.

<Step S650>

The partial image adaptability determination unit 1424 calculates an adaptability value indicating whether the partial image selected with reference to image features of the partial image candidates is an appropriate image. In the present exemplary embodiment, the partial image adaptability determination unit 1424 uses a value indicating the sharpness of the partial image as the adaptability value. If the calculated adaptability value is equal to or greater than a predetermined value, the partial image adaptability determination unit 1424 recognizes the selected partial image as an adaptable partial image.

If it is determined that the selected partial image is inadaptable, the processing returns to step S630 to change the eye part feature parameters and repeat the processing in step S640 and step S650 until it is determined that the selected partial image is adaptable.

The image processing apparatus having the above-described configuration can select a group of SLO partial images whose focus positions are set to be adjacent to the retinal inner layer boundary deformed greatly due to myopia at each position on the eyeground. Further, the image processing apparatus can generate a new SLO image by combining and integrating the selected SLO partial images. Thus, it is feasible to obtain an image easy to observe or analyze the distribution of the nerve fiber bundle in the imaging range even when the shape of the retinal inner layer boundary is deformed greatly due to myopia.

In a third exemplary embodiment, the observation (analysis) target is a retinal (capillary) blood vessel in cases of diabetic retinopathy.

The image processing apparatus selects partial images having focus positions set to be adjacent to a target retinal inner layer boundary, at each position on the eyeground, based on information of the retinal inner layer boundary acquired from an OCT volume image, from the same group of SLO images captured at various focus positions. The image processing apparatus connects the selected partial images to generate an SLO still image focused on the retinal blood vessel.

Further, if an operator designates an arbitrary position of the capillary vessel on the SLO still image, the image processing apparatus displays a moving image of a partial area that corresponds to the instructed position to enable the operator to observe and analyze the state of blood flow easily.

Thus, even if the shape of the target retinal inner layer boundary is deformed greatly due to diabetic macular edema, the operator can easily observe or analyze the distribution of the retinal blood vessel and the state of blood flow.

A functional block diagram of the image processing apparatus 10 according to the present exemplary embodiment is similar to that (see FIG. 9) described in the second exemplary embodiment. Further, image generation processing according to the present exemplary embodiment is similar to that (see FIG. 12) described in the second exemplary embodiment.

Processing to be performed in step S1230, step S1260, step S1270, and step S1280 is similar to the processing described in the first exemplary embodiment, therefore its description is omitted. Processing to be performed in step S1200, step S1210, step S1220, step S1240, and step S1250 according to the present exemplary embodiment is described in detail below.

<Step S1200>

Figure 14A:
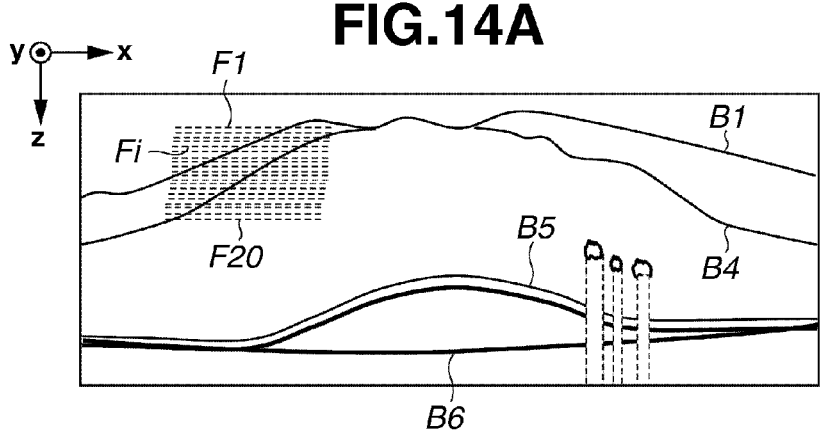

The eye part volume image acquisition unit 111 captures an eye part volume image and transmits the eye part volume image to the structure acquisition unit 120. The eye part volume image acquired in the present exemplary embodiment includes a macula area as illustrated in FIG. 14A, in which the retinal inner layer boundary is deformed due to macular edema.

<Step S1210>

The structure acquisition unit 120 acquires eye part features from the eye part volume image acquired by the eye part volume image acquisition unit 111. In the present exemplary embodiment, it is presumed that an observation (or analysis) target instructed beforehand by the instruction acquisition unit 150 is the capillary vessel.

The eye part features extracted by the structure acquisition unit 120 include the inner limiting membrane B1, the nerve fiber layer boundary B2, the inner plexiform layer boundary B4, the interface between inner and outer segments of the photoreceptors B5, the outer boundary of the retinal pigment epithelium B6, and the retinal blood vessel (not illustrated). The structure acquisition unit 120 can use a layer boundary and retinal blood vessel extraction method that is similar to the method described in the first exemplary embodiment (see step S410).

<Step S1220>

The SLO image acquisition unit 110 adjusts the focus position based on the layer boundaries acquired by the structure acquisition unit 120 in step S1210 and captures a group of aberration corrected SLO images. In the present exemplary embodiment, the SLO image acquisition unit 110 sets a variation range with respect to the focus position center based on a variation range of each of the nerve fiber layer boundary B2 and the inner plexiform layer boundary B4 in the z coordinate (see FIG. 14A) and sets a variation interval of 5 μm.

Example images that can be obtained through the above-described processing are described below with reference to FIGS. 14A to 14D. FIG. 14A illustrates an OCT tomographic image of the macula area captured by the composite apparatus 200. Further, Fi (F1 through F20) represents the imaging position of each SLO image.

Figure 14B:
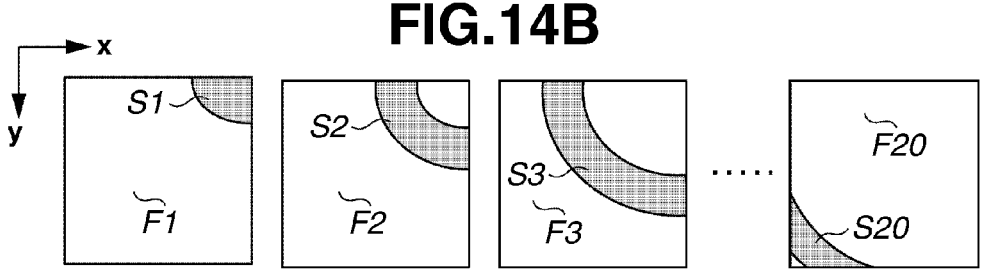
Figure 14C:
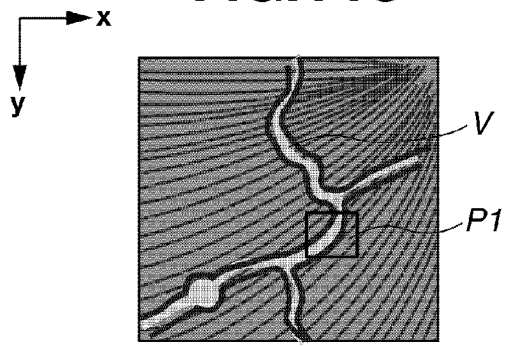

FIG. 14B illustrates SLO images selected by the selection unit 142. The SLO image positioned at the left side of FIG. 14B has the focus position adjacent to the front side. The selection unit 142 selects observation (measurement) target areas whose focus positions are appropriately set as partial images Si. The image generation unit 143 combines these partial areas Si to obtain an integrated image of the nerve fiber bundle illustrated in FIG. 14C. Thus, even when the shape of the retinal inner layer is deformed greatly, the image generation unit 143 can obtain an SLO still image easy to observe and analyze the shape of the capillary vessel in the imaging range.

Further, if a user points an arbitrary position of the capillary vessel included in the SLO still image via the input unit 180, the instruction acquisition unit 150 acquires a position designation instruction. The image generation unit 143 generates a partial image candidate group in the vicinity of the designated position (see P1 in FIG. 14C), which is displayed as a moving image as illustrated in FIG. 14D.

Figure 14D:
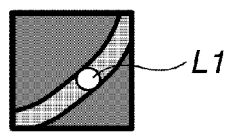

A user can observe a moving white blood cell L1 on the partial moving image, as illustrated in FIG. 14D. In the present exemplary embodiment, the moving image displayed in this case is the group of partial images acquired in step S630 and step S650, which are usable to constitute a moving image because respective partial image candidates are different from each other in shooting time.

Next, example processing to be executed in step S1240 is described in detail below with reference to the flowchart illustrated in FIG. 6 and the images illustrated in FIGS. 14A to 14D.

<Step S610>

The selection unit 142 acquires the eye part features (including the inner limiting membrane B1, the nerve fiber layer boundary B2, the inner plexiform layer boundary B4, the interface between inner and outer segments of the photoreceptors B5, the inner boundary of the retinal pigment epithelium B6, and the retinal blood vessel area V) acquired in step S410.

<Step S620>

The parameter setting unit 1421 sets the following parameters relating to SLO partial image selection method based on the distribution of the eye part features acquired in step S610.

(i) determination whether to combine a plurality of partial images or use a single SLO image (ii) parameter usable in partial image selection (iii) number of partial image candidates to be selected (iv) determination whether to execute combination processing if there is a plurality of partial image candidates (v) determination whether to set adaptability for each partial image With respect to the parameter (i), the image processing apparatus according to the present exemplary embodiment determines that the observation target (i.e., the inner plexiform layer boundary B4) is deformed greatly as illustrated in FIG. 14A. Therefore, the processing proceeds to step S630 to select partial images different in focus position at each position (x, y) in the imaging range.

A method for determining the degree of bending in layer shape used in the present exemplary embodiment is similar to the method described in the first exemplary embodiment, therefore its description is omitted.

With respect to the parameter (ii), the image processing apparatus according to the present exemplary embodiment selects images whose focus position center is set to be less than a predetermined value in distance from the inner plexiform layer boundary B4 as partial images. In the present exemplary embodiment, the parameter (ii) is set to be 50 μm as the distance from the nerve fiber layer boundary.

With respect to the parameter (iii), the image processing apparatus according to the present exemplary embodiment acquires a group of SLO images at a plurality of focus positions spaced at the intervals of 5 μm. Therefore, the number of partial image candidates is twenty.

With respect to the parameter (iv), the image processing apparatus determines whether to perform combination processing if there is a plurality of partial image candidates. In the present exemplary embodiment, the image processing apparatus performs the combination processing in response to an instruction input beforehand by a user via the instruction acquisition unit 150.

With respect to the parameter (v), the image processing apparatus determines an adaptability value based on an instruction having been input beforehand by a user via the instruction acquisition unit 150.

<Step S630>

To set the focus position to be adjacent to the observation target (i.e., the inner plexiform layer boundary B4) at each position on the eyeground, the partial image candidate selection unit 1422 selects partial images whose focus positions are adjusted to be adjacent to the bent inner plexiform layer boundary. As having been obtained for the parameters (ii) and (iii) in step S620, the partial image candidate selection unit 1422 selects twenty partial images as partial image candidates because the distance from the inner plexiform layer boundary B4 is less than 50 μm.

The target to be focused is not limited to a specific layer boundary and can be a retinal blood vessel or a lesion in the retina.

<Step S640>

The integration unit 1423 performs combination processing using the partial image candidates selected in step S630, based on the determination result with respect to the parameter (iv) in step S620.

<Step S650>

The partial image adaptability determination unit 1424 calculates an adaptability value indicating whether the partial image selected with reference to image features of the partial image candidates is an appropriate image. In the present exemplary embodiment, the partial image adaptability determination unit 1424 uses a value indicating the sharpness of the partial image as the adaptability value. If the calculated adaptability value is equal to or greater than a predetermined value, the partial image adaptability determination unit 1424 recognizes the selected partial image as an adaptable partial image.

If it is determined that the selected partial image is inadaptable, the processing returns to step S630 to change the eye part feature parameters and repeat the processing in step S640 and step S650 until it is determined that the selected partial image is adaptable.

In the present exemplary embodiment, the selection unit selects two types of images as partial images. More specifically, the selection unit selects the partial images combined in step S640 for SLO still image generation and the group of partial images acquired in step S630 and step S650 for SLO partial moving image generation.

Similar to the first or second exemplary embodiment, it is feasible to skip step S650 when the processing proceeds to step S450.

Next, the processing to be executed in step S1150 is described in detail below with reference to the flowchart illustrated in FIG. 8 and the images illustrated in FIGS. 14A to 14D.

<Step S810>

The connection unit 1431 generates an SLO still image candidate by connecting the partial images corresponding to respective positions on the eyeground, which have been selected in step S650, along a plane extending in the x and y directions.

As described above, in a case where the processing skips step S640 or step S650 and directly proceeds to step S810, the connection unit 1431 selects a predetermined combination of partial images, among respective eyegrounds, and connects the selected partial images along the plane extending in the x and y directions.

<Step S820>

The SLO image adaptability determination unit 1432 determines whether the SLO image candidate generated in step S810 is adaptable to the observation (analysis). In the present exemplary embodiment, the SLO image adaptability determination unit 1432 measures the S/N ratio and the sharpness of respective partial images to determine the degree of dispersion in observation (analysis) conditions between the partial images.

If both values satisfy the condition that a sum of square errors of respective partial images is less than a predetermined value, the SLO image adaptability determination unit 1432 determines that the image generated in step S810 is adaptable. The processing proceeds to step S830.

On the contrary, if at least one of the measured values is equal to or greater than a predetermined value, the SLO image adaptability determination unit 1432 determines that the image generated in step S810 is inadaptable. In this case, the processing returns to step S810. The SLO image adaptability determination unit 1432 changes the combination of partial image candidates and performs the above-described processing in step S820 again until the adaptability is confirmed.

<Step S830>

The correction unit 1433 calculates a change amount in pixel value and smoothness in edge shape at a boundary area of each selected partial area of the SLO images selected in step S820. In the present exemplary embodiment, for example, dispersion values obtainable as the smoothness in edge shape by performing arbitrary known edge detection processing, with respect to the angle between edge forming control points, and the change amount in pixel value in the direction perpendicular to the boundary area are usable. If the change amount in density or shape is equal to or greater than a predetermined value, the correction unit 1433 performs luminance adjustment for the boundary area.

As described above, the observation (analysis) target is the retina capillary vessel in cases of diabetic retinopathy. The image processing apparatus selects a group of SLO partial images whose focus positions are set to be adjacent to the retinal inner layer at each position on the eyeground having a greatly deformed retinal inner layer due to diabetic retinopathy. The image processing apparatus generates a new SLO still image by combining and connecting the selected SLO partial images.

Further, if a user points an arbitrary position of the capillary vessel included in the SLO still image, the image processing apparatus displays a partial moving image corresponding to a pointed area to enable the user to easily observe and analyze the state of blood flow.

Thus, even when the shape of the retinal inner layer boundary is deformed greatly due to diabetic macular edema, the image processing apparatus can obtain an SLO image easy to observe or analyze the distribution of the retinal blood vessel and the state of blood flow in the imaging range.

In the above-described exemplary embodiment, the image processing apparatus acquires still and moving images of a retina having been captured beforehand. However, it is useful to realize a real-time display of the acquired still and moving images during a shooting operation of the retina. In this case, the SLO image capturing apparatus 30 repetitively acquires SLO images at predetermined focus positions and the image processing apparatus 90 periodically performs image processing.

Further, to obtain a moving image easy to observe, it is useful to capture a plurality of SLO images at predetermined focus positions. The display control unit 160 can cause the display unit 170 to display these images successively to realize the display of a moving image.

An image processing apparatus according to a fourth exemplary embodiment can analyze the specific structure of each observation target described in the first to third exemplary embodiments. The image processing apparatus according to the fourth exemplary embodiment sets shooting parameters and image processing parameters according to a user input designating one of the observation targets to carry out the shooting.

Further, hardware and functional configurations according to the fourth exemplary embodiment are similar to those described in the second exemplary embodiment. The configurations are also applicable to those described in the first exemplary embodiment.

A user selects an observation target via the input unit 180. The instruction acquisition unit 150 designates the selected observation target. The instruction unit 190 sets the shooting parameters (e.g., focus position and focus interval) according to the designated observation target.

Further, the object image acquisition unit 140 sets the image processing parameters based on the designated observation target. For example, if the observation target is the photoreceptor cell of the macula area described in the first exemplary embodiment, the object image acquisition unit 140 sets the shooting position of each SLO image to be adjacent to the interface between inner and outer segments of the photoreceptors in the macula area and further sets the focus positions at the interval of 20 μm.

If the observation target is the nerve fiber bundle of the optic disc area described in the second exemplary embodiment, the object image acquisition unit 140 sets the shooting position of each SLO image to be adjacent to the optic disc area and further sets the focus positions at the interval of 5 μm. The shooting parameters can be set similarly for each OCT image.

In a case where the configuration described in the first exemplary embodiment is employed, the object image acquisition unit 140 sets only the image processing parameters if the captured images are processed.

When the above-described processing is performed, the observation target position can be designated in response to a user input and the shooting parameters or the image processing parameters can be automatically set. Therefore, the work efficiency can be improved.

Other Exemplary Embodiments

A computer including a CPU capable of executing a software program can realize each of the above-described image processing apparatuses 10 and 90. Alternatively, it is useful to provide a circuit that can realize each functional block of the image processing apparatuses 10 and 90. In this case, each circuit may not correspond to the entire functional block and may correspond to only a part of the corresponding function.

Further, each of the image processing apparatuses 10 and 90 can be an image processing system constituted by a plurality of devices.

In the above-described exemplary embodiments, the structure acquisition unit 120 of the image processing apparatuses 10 and 90 acquires features from an OCT tomographic image. However, any another imaging or diagnostic apparatus is usable to identify the structure of an observation target. For example, it is useful to identify the organization structure of the observation target by analyzing each of a plurality of SLO images and combine a plurality of selected partial images or select an appropriate SLO image. Further, any other modality (e.g., an imaging apparatus or a measurement apparatus) is employable to identify the organization structure.

The image processing apparatus 10 according to the first exemplary embodiment acquires an image of a specific structure based on SLO images captured beforehand and stored in the data server 50. Alternatively, the images can be directly acquired from the SLO image capturing apparatus 30 as described in the second and third exemplary embodiments. Further, the image processing apparatus 10 can be configured to perform various processing (e.g., settings of shooting conditions, correction, and shooting instruction) for each imaging apparatus.

Further, the input unit 180 of the image processing apparatuses 10 and 90 can be configured to receive an instruction from an inspection order management system in addition to an instruction from a user. Alternatively, the input unit 180 can be replaced by the inspection order management system. In short, an appropriate apparatus capable of inputting information required to set the image processing parameters for the image processing apparatus 10 or 90, or the shooting parameters for the image processing apparatus 90, is employable.

The image processing apparatuses 10 and 90 determines whether to combine selected partial images or select an appropriate SLO image with reference to a deformation state of a target to be captured. Alternatively, it is feasible to omit the above-described determination processing if the image processing apparatuses 10 and 90 are configured to perform either one of the two operations. For example, regardless of the deformation state, it is useful to obtain an integrated image of a specific structure by combining partial images that can be obtained through the processing in step S630 and the following steps illustrated in FIG. 6.

In the above-described exemplary embodiment, to identify an in-focused state, the image processing apparatus determines whether the distance from a specific structure is within a predetermined range. However, it is also useful to acquire a partial image from an SLO image closest to the specific structure at each position of the specific structure.

Further, in the above-described exemplary embodiment, the image processing apparatus selects a partial image having better quality from the in-focused images determined in step S440. Moreover, it is also useful to select a partial image having a highest value in adaptability from all SLO images, considering focus matching degree and image quality.

As described above, the image processing apparatus according to the present embodiment can obtain an SLO image focused on a specific structure from a group of SLO images captured at various focus positions and can observe the specific structure easily.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-040273 filed Feb. 25, 2011, which is hereby incorporated by reference herein in its entirety.

What is claimed is:

1. An image processing apparatus comprising:
a Scanning Laser Ophthalmoscope (SLO) image acquisition unit configured to acquire a plurality of SLO images obtained by an SLO apparatus that scans a target to be captured with signal light at various focus positions in an optical axis direction of the signal light;
a structure acquisition unit configured to acquire a specific structure of the target to be captured;
a selection unit configured to select a plurality of partial images focused on the specific structure from the plurality of SLO images according to the specific structure; and
an object image generation unit configured to generate an integrated image of the specific structure by combining the plurality of partial images.

2. The image processing apparatus according to claim 1, wherein the object image generation unit generates the integrated image that the specific structure continues based on the plurality of SLO images captured at various focus positions.

3. The image processing apparatus according to claim 1, wherein the selection unit selects a partial image corresponding to each of a plurality of partial areas of the specific structure based on a plurality of SLO images whose focus positions are less than a predetermined threshold in distance from the partial area.

4. The image processing apparatus according to claim 3, wherein if there is a plurality of SLO images whose focus positions are less than the predetermined threshold in distance from the partial area, the object image generation unit combines the plurality of SLO images to generate an integrated partial image corresponding to each partial area.

5. The image processing apparatus according to claim 1, wherein the selection unit selects a partial image corresponding to each partial area of the specific structure from the plurality of SLO images and the object image generation unit generates the integrated image by combining the acquired partial images if the degree of bending of the specific structure is large, and the selection unit selects an optimum SLO image that fits the specific structure from the plurality of SLO images if the degree of bending is small.

6. The image processing apparatus according to claim 1, further comprising:
a correction unit configured to correct the focus position or a focus position interval of the signal light emitted by the SLO apparatus based on the acquired SLO images and the specific structure; and
an instruction unit configured to instruct capturing an SLO image of the target to be captured with the signal light at the corrected focus position.

7. The image processing apparatus according to claim 1, further comprising:
a display control unit configured to display the integrated image of the specific structure.

8. The image processing apparatus according to claim 7, further comprising:
a designation unit configured to designate a position on a still image of the specific structure,
wherein the display control unit is configured to display a moving image that corresponds to the designated position.

9. The image processing apparatus according to claim 1, further comprising:
a designation unit configured to designate the specific structure, and
a setting unit configured to set a parameter required in acquiring the image of the specific structure from the plurality of SLO images captured at various focus positions, according to the designated structure.

10. The image processing apparatus according to claim 1, wherein the structure acquisition unit is configured to acquire the specific structure of the target to be captured based on a tomographic image of the target captured by an OCT imaging apparatus.

11. The image processing apparatus according to claim 1, wherein the SLO apparatus includes an adaptive optics system having aberration correction capability.

12. An image processing system comprising:
the image processing apparatus according to claim 1, and
a display unit configured to display an image of the specific structure acquired by the image processing apparatus.

13. An image processing method comprising:
acquiring a plurality of SLO images obtained by a SLO apparatus that scans a target to be captured with signal light at various focus positions in an optical axis direction of the signal light;
acquiring a specific structure of the target to be captured;
selecting a plurality of partial images focused on the specific structure from the plurality of SLO images according to the specific structure; and
generating an integrated image of the specific structure by combining the plurality of partial images.

* * * * *